US008404300B2

(12) United States Patent
Wang

(10) Patent No.: US 8,404,300 B2
(45) Date of Patent: *Mar. 26, 2013

(54) DRUG RELEASING COATINGS FOR MEDICAL DEVICES

(75) Inventor: Lixiao Wang, Medina, MN (US)

(73) Assignee: Lutonix, Inc., New Hope, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/042,218

(22) Filed: Mar. 7, 2011

(65) Prior Publication Data

US 2011/0159169 A1 Jun. 30, 2011

Related U.S. Application Data

(62) Division of application No. 11/942,452, filed on Nov. 19, 2007.

(60) Provisional application No. 60/860,084, filed on Nov. 20, 2006, provisional application No. 60/880,742, filed on Jan. 17, 2007, provisional application No. 60/897,427, filed on Jan. 25, 2007, provisional application No. 60/903,529, filed on Feb. 26, 2007, provisional application No. 60/926,850, filed on Apr. 30, 2007, provisional application No. 60/904,473, filed on Mar. 2, 2007, provisional application No. 60/891,380, filed on Oct. 19, 2007, provisional application No. 60/981,384, filed on Oct. 19, 2007.

(51) Int. Cl.
*B05D 5/00* (2006.01)
*B05D 3/02* (2006.01)
*B05D 1/02* (2006.01)
*B05D 1/18* (2006.01)
*A61K 9/00* (2006.01)
*A61K 31/436* (2006.01)
*A61K 31/337* (2006.01)
*A61P 9/00* (2006.01)

(52) U.S. Cl. ........ 427/2.25; 427/2.31; 427/2.1; 427/2.3; 514/291; 514/449; 424/422; 424/400

(58) Field of Classification Search .................. None
See application file for complete search history.

(56) References Cited

U.S. PATENT DOCUMENTS

| | | | |
|---|---|---|---|
| 3,929,992 A | 12/1975 | Sehgal et al. |
| 3,993,749 A | 11/1976 | Sehgal et al. |
| 4,316,885 A | 2/1982 | Rakhit |
| 4,364,921 A | 12/1982 | Speck et al. |
| 4,921,483 A | 5/1990 | Wijay et al. |
| 5,023,262 A | 6/1991 | Caufield et al. |
| 5,023,263 A | 6/1991 | Von Burg |
| 5,023,264 A | 6/1991 | Caufield et al. |
| 5,026,607 A | 6/1991 | Kiezulas |
| 5,061,738 A | 10/1991 | Solomon et al. |
| 5,080,899 A | 1/1992 | Sturm et al. |
| 5,092,841 A | 3/1992 | Spears |
| 5,100,883 A | 3/1992 | Schiehser |
| 5,102,402 A | 4/1992 | Dror et al. |
| 5,102,876 A | 4/1992 | Caufield |
| 5,118,677 A | 6/1992 | Caufield |
| 5,118,678 A | 6/1992 | Kao et al. |
| 5,120,322 A | 6/1992 | Davis et al. |
| 5,120,725 A | 6/1992 | Kao et al. |
| 5,120,726 A | 6/1992 | Failli et al. |
| 5,120,727 A | 6/1992 | Kao et al. |
| 5,120,842 A | 6/1992 | Failli et al. |
| 5,130,307 A | 7/1992 | Failli et al. |
| 5,135,516 A | 8/1992 | Sahatjian et al. |
| 5,138,051 A | 8/1992 | Hughes et al. |
| 5,151,413 A | 9/1992 | Caufield et al. |
| 5,162,333 A | 11/1992 | Failli et al. |
| 5,164,399 A | 11/1992 | Failli et al. |
| 5,177,203 A | 1/1993 | Failli et al. |
| 5,194,447 A | 3/1993 | Kao |
| 5,196,596 A | 3/1993 | Abatjoglou |
| 5,199,951 A | 4/1993 | Spears |
| 5,221,670 A | 6/1993 | Caufield |
| 5,221,740 A | 6/1993 | Hughes |
| 5,233,036 A | 8/1993 | Hughes |
| 5,252,579 A | 10/1993 | Skotnicki et al. |
| 5,254,089 A | 10/1993 | Wang et al. |
| 5,260,300 A | 11/1993 | Hu |
| 5,262,423 A | 11/1993 | Kao |
| 5,269,770 A | 12/1993 | Conway et al. |
| 5,302,584 A | 4/1994 | Kao et al. |
| 5,304,121 A | 4/1994 | Sahatjian |
| 5,324,261 A | 6/1994 | Amundson et al. |
| 5,346,893 A | 9/1994 | Failli et al. |
| 5,349,060 A | 9/1994 | Kao et al. |
| 5,362,718 A | 11/1994 | Skotnicki et al. |
| 5,370,614 A | 12/1994 | Amundson et al. |
| 5,373,014 A | 12/1994 | Failli et al. |
| 5,378,696 A | 1/1995 | Caufield |

(Continued)

FOREIGN PATENT DOCUMENTS

DE 101 15 740 10/2002
EP 0 519 063 12/1992

(Continued)

OTHER PUBLICATIONS

European Search Report for EP 09156858, Jul. 21, 2009.

(Continued)

*Primary Examiner* — Suzanne Ziska

(74) *Attorney, Agent, or Firm* — Dinsmore & Shohl, LLP

(57) ABSTRACT

The invention relates to a medical device for delivering a therapeutic agent to a tissue. The medical device has a layer overlying the exterior surface of the medical device. The layer contains a therapeutic agent and an additive. The additive has a hydrophilic part and a hydrophobic part and the therapeutic agent is not enclosed in micelles or encapsulated in particles or controlled release carriers.

16 Claims, 2 Drawing Sheets

U.S. PATENT DOCUMENTS

| | | |
|---|---|---|
| 5,378,836 A | 1/1995 | Kao et al. |
| 5,380,298 A | 1/1995 | Zabetakis et al. |
| 5,380,299 A | 1/1995 | Fearnot et al. |
| 5,385,908 A | 1/1995 | Nelson et al. |
| 5,385,909 A | 1/1995 | Nelson et al. |
| 5,385,910 A | 1/1995 | Ocain et al. |
| 5,387,680 A | 2/1995 | Nelson |
| 5,389,639 A | 2/1995 | Failli et al. |
| 5,391,730 A | 2/1995 | Skotnicki et al. |
| 5,411,967 A | 5/1995 | Kao et al. |
| 5,441,759 A | 8/1995 | Crouther et al. |
| 5,446,048 A | 8/1995 | Failli et al. |
| 5,463,048 A | 10/1995 | Skotnicki et al. |
| 5,464,650 A | 11/1995 | Berg et al. |
| 5,480,988 A | 1/1996 | Failli et al. |
| 5,480,989 A | 1/1996 | Kao et al. |
| 5,482,945 A | 1/1996 | Armstrong et al. |
| 5,489,680 A | 2/1996 | Failli et al. |
| 5,490,839 A | 2/1996 | Wang et al. |
| 5,491,231 A | 2/1996 | Nelson et al. |
| 5,496,276 A | 3/1996 | Wang et al. |
| 5,504,091 A | 4/1996 | Molnar-Kimber et al. |
| 5,504,204 A | 4/1996 | Failli et al. |
| 5,508,399 A | 4/1996 | Kao et al. |
| 5,509,899 A | 4/1996 | Fan et al. |
| 5,516,781 A | 5/1996 | Morris et al. |
| 5,525,348 A | 6/1996 | Whitbourne et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,559,121 A | 9/1996 | Harrison et al. |
| 5,559,227 A | 9/1996 | Failli et al. |
| 5,563,145 A | 10/1996 | Failli et al. |
| 5,563,146 A | 10/1996 | Morris |
| 5,567,709 A | 10/1996 | Skotnicki et al. |
| 5,573,518 A | 11/1996 | Haaga |
| 5,599,307 A | 2/1997 | Bacher et al. |
| 5,607,463 A | 3/1997 | Schwartz et al. |
| 5,609,629 A | 3/1997 | Fearnot et al. |
| 5,616,608 A | 4/1997 | Kinsella et al. |
| 5,632,772 A | 5/1997 | Alcime et al. |
| 5,674,192 A | 10/1997 | Sahatjian et al. |
| 5,674,287 A | 10/1997 | Slepian et al. |
| 5,679,400 A | 10/1997 | Tuch |
| 5,693,034 A | 12/1997 | Buscemi et al. |
| 5,698,582 A | 12/1997 | Bastart et al. |
| 5,702,754 A | 12/1997 | Zhong |
| 5,716,981 A | 2/1998 | Hunter et al. |
| 5,733,925 A | 3/1998 | Kunz et al. |
| 5,738,901 A | 4/1998 | Wang et al. |
| 5,752,930 A | 5/1998 | Rise et al. |
| 5,766,158 A | 6/1998 | Opolski |
| 5,776,184 A | 7/1998 | Tuch |
| 5,776,943 A | 7/1998 | Christians et al. |
| 5,780,462 A | 7/1998 | Lee et al. |
| 5,797,887 A | 8/1998 | Rosen et al. |
| 5,807,306 A | 9/1998 | Shapland et al. |
| 5,824,049 A | 10/1998 | Ragheb et al. |
| 5,827,289 A | 10/1998 | Reiley et al. |
| 5,843,089 A | 12/1998 | Sahatjian et al. |
| 5,865,814 A | 2/1999 | Tuch |
| 5,868,719 A | 2/1999 | Tsukernik |
| 5,869,127 A | 2/1999 | Zhong |
| 5,873,904 A | 2/1999 | Ragheb et al. |
| 5,879,697 A | 3/1999 | Ding et al. |
| 5,893,840 A | 4/1999 | Hull et al. |
| 5,919,145 A | 7/1999 | Sahatjian |
| 5,919,570 A | 7/1999 | Hostettler et al. |
| 5,922,730 A | 7/1999 | Hu et al. |
| 5,947,977 A | 9/1999 | Slepian et al. |
| 5,954,706 A | 9/1999 | Sahatjian |
| 5,977,163 A | 11/1999 | Li |
| 5,981,568 A | 11/1999 | Kunz et al. |
| 5,985,325 A | 11/1999 | Nagi |
| 5,989,591 A | 11/1999 | Nagi |
| 6,015,809 A | 1/2000 | Zhu et al. |
| 6,039,721 A | 3/2000 | Johnson et al. |
| 6,042,875 A | 3/2000 | Ding et al. |
| 6,046,230 A * | 4/2000 | Chung et al. .................. 514/449 |
| 6,050,980 A | 4/2000 | Wilson |
| 6,056,722 A | 5/2000 | Jayaraman |
| 6,074,659 A | 6/2000 | Kunz et al. |
| 6,096,070 A | 8/2000 | Ragheb et al. |
| 6,120,904 A | 9/2000 | Hostettler et al. |
| 6,129,705 A | 10/2000 | Grantz |
| 6,143,037 A | 11/2000 | Goldstein et al. |
| 6,146,358 A | 11/2000 | Rowe |
| 6,176,849 B1 | 1/2001 | Yang et al. |
| 6,218,016 B1 | 4/2001 | Tedeschi et al. |
| 6,221,467 B1 | 4/2001 | Nazarova et al. |
| 6,228,393 B1 | 5/2001 | DiCosmo et al. |
| 6,248,363 B1 | 6/2001 | Patel et al. |
| 6,261,630 B1 | 7/2001 | Nazarova et al. |
| 6,280,411 B1 | 8/2001 | Lennox |
| 6,294,192 B1 | 9/2001 | Patel et al. |
| 6,299,604 B1 | 10/2001 | Ragheb et al. |
| 6,299,980 B1 | 10/2001 | Shah et al. |
| 6,306,144 B1 | 10/2001 | Sydney et al. |
| 6,306,166 B1 | 10/2001 | Barry et al. |
| 6,312,406 B1 | 11/2001 | Jayaraman |
| 6,328,970 B1 | 12/2001 | Molnar-Kimber et al. |
| 6,331,547 B1 | 12/2001 | Zhu et al. |
| 6,335,029 B1 | 1/2002 | Kamath et al. |
| 6,364,856 B1 | 4/2002 | Ding et al. |
| 6,364,893 B1 | 4/2002 | Sahatjian et al. |
| 6,369,039 B1 | 4/2002 | Palasis et al. |
| 6,395,326 B1 | 5/2002 | Castro et al. |
| 6,409,716 B1 | 6/2002 | Sahatjian et al. |
| 6,419,692 B1 | 7/2002 | Yang et al. |
| 6,432,973 B1 | 8/2002 | Zhu et al. |
| 6,443,941 B1 | 9/2002 | Slepian et al. |
| 6,444,324 B1 | 9/2002 | Yang et al. |
| 6,458,138 B1 | 10/2002 | Sydney et al. |
| 6,506,408 B1 | 1/2003 | Palasis |
| 6,524,274 B1 | 2/2003 | Rosenthal et al. |
| 6,528,150 B2 | 3/2003 | Nazarova et al. |
| 6,544,544 B2 | 4/2003 | Hunter et al. |
| 6,571,125 B2 | 5/2003 | Thompson |
| 6,576,224 B1 | 6/2003 | Osbakken et al. |
| 6,589,215 B2 | 7/2003 | Yang et al. |
| 6,589,546 B2 | 7/2003 | Kamath et al. |
| 6,592,548 B2 | 7/2003 | Jayaraman |
| 6,610,035 B2 | 8/2003 | Yang et al. |
| 6,616,650 B1 | 9/2003 | Rowe |
| 6,656,156 B2 | 12/2003 | Yang et al. |
| 6,677,357 B2 | 1/2004 | Zhu et al. |
| 6,680,330 B2 | 1/2004 | Zhu et al. |
| 6,682,545 B1 | 1/2004 | Kester |
| 6,699,272 B2 | 3/2004 | Slepian et al. |
| 6,730,064 B2 | 5/2004 | Ragheb et al. |
| 6,774,278 B1 | 8/2004 | Ragheb et al. |
| 6,890,339 B2 | 5/2005 | Sahatjian et al. |
| 6,890,546 B2 | 5/2005 | Mollison et al. |
| 6,893,431 B2 | 5/2005 | Naimark et al. |
| 6,899,731 B2 | 5/2005 | Li et al. |
| 6,918,869 B2 | 7/2005 | Shaw et al. |
| 6,921,390 B2 | 7/2005 | Bucay-Couto et al. |
| 6,939,320 B2 | 9/2005 | Lennox |
| 6,958,153 B1 | 10/2005 | Ormerod et al. |
| 6,991,809 B2 | 1/2006 | Anderson |
| 6,997,949 B2 | 2/2006 | Tuch |
| 7,008,411 B1 | 3/2006 | Mandrusov et al. |
| 7,025,752 B2 | 4/2006 | Rice et al. |
| 7,048,714 B2 | 5/2006 | Richter |
| 7,056,550 B2 | 6/2006 | Davila et al. |
| 7,060,051 B2 | 6/2006 | Palasis |
| 7,066,904 B2 | 6/2006 | Rosenthal et al. |
| 7,077,859 B2 | 7/2006 | Sirhan et al. |
| 7,108,684 B2 | 9/2006 | Farnan |
| 7,144,419 B2 | 12/2006 | Cheng et al. |
| 7,153,957 B2 | 12/2006 | Chew et al. |
| 7,160,317 B2 | 1/2007 | McHale et al. |
| 7,163,555 B2 | 1/2007 | Dinh |
| 7,172,619 B2 | 2/2007 | Richter |
| 7,175,873 B1 | 2/2007 | Roorda et al. |

| | | |
|---|---|---|
| 7,176,261 B2 | 2/2007 | Tijsma et al. |
| 7,179,251 B2 | 2/2007 | Palasis |
| 7,198,637 B2 | 4/2007 | Deshmukh et al. |
| 7,208,009 B2 | 4/2007 | Richter |
| 7,214,198 B2 | 5/2007 | Greco et al. |
| 7,226,586 B2 | 6/2007 | Fitzhugh et al. |
| 7,232,573 B1 | 6/2007 | Ding |
| 7,235,096 B1 | 6/2007 | Van Tassel et al. |
| 7,244,444 B2 | 7/2007 | Bates |
| 7,247,313 B2 | 7/2007 | Roorda et al. |
| 7,282,213 B2 | 10/2007 | Schroeder et al. |
| 7,285,304 B1 | 10/2007 | Hossainy et al. |
| 7,292,885 B2 | 11/2007 | Scott et al. |
| 7,294,329 B1 | 11/2007 | Ding |
| 7,306,580 B2 | 12/2007 | Paul et al. |
| 7,507,433 B2 | 3/2009 | Weber |
| 7,524,527 B2 | 4/2009 | Stenzel |
| 7,547,294 B2 | 6/2009 | Seward et al. |
| 2001/0002435 A1 | 5/2001 | Berg et al. |
| 2001/0018072 A1 | 8/2001 | Unger |
| 2001/0034363 A1 | 10/2001 | Li et al. |
| 2002/0010419 A1 | 1/2002 | Jayaraman |
| 2002/0039594 A1 | 4/2002 | Unger |
| 2002/0077684 A1 | 6/2002 | Clemens et al. |
| 2002/0082552 A1 | 6/2002 | Ding et al. |
| 2002/0095114 A1 | 7/2002 | Palasis |
| 2002/0098278 A1 | 7/2002 | Bates |
| 2002/0099332 A1 | 7/2002 | Slepian et al. |
| 2002/0102280 A1 | 8/2002 | Anderson |
| 2002/0138048 A1 | 9/2002 | Tuch |
| 2002/0151844 A1 | 10/2002 | Yang et al. |
| 2002/0183380 A1 | 12/2002 | Hunter |
| 2002/0192280 A1 | 12/2002 | Hunter |
| 2003/0004209 A1 | 1/2003 | Hunter et al. |
| 2003/0045587 A1 | 3/2003 | Anderson |
| 2003/0064965 A1 | 4/2003 | Richter |
| 2003/0100577 A1 | 5/2003 | Zhu et al. |
| 2003/0100886 A1 | 5/2003 | Segal et al. |
| 2003/0100887 A1 | 5/2003 | Scott et al. |
| 2003/0114477 A1 | 6/2003 | Zhu et al. |
| 2003/0114791 A1 | 6/2003 | Rosenthal et al. |
| 2003/0157032 A1 | 8/2003 | Cavaillon et al. |
| 2003/0157161 A1 | 8/2003 | Hunter |
| 2003/0207936 A1 | 11/2003 | Chen |
| 2003/0216699 A1 | 11/2003 | Falotico |
| 2003/0235602 A1 | 12/2003 | Schwarz |
| 2004/0018296 A1 | 1/2004 | Castro et al. |
| 2004/0037886 A1 | 2/2004 | Hsu |
| 2004/0062810 A1 | 4/2004 | Hunter |
| 2004/0073284 A1 | 4/2004 | Bates et al. |
| 2004/0076672 A1 | 4/2004 | Hunter |
| 2004/0077677 A1 | 4/2004 | Ashraf et al. |
| 2004/0087902 A1 | 5/2004 | Richter |
| 2004/0127551 A1* | 7/2004 | Zhang et al. ............... 514/449 |
| 2004/0156816 A1 | 8/2004 | Anderson |
| 2004/0167152 A1 | 8/2004 | Rubino et al. |
| 2004/0176339 A1 | 9/2004 | Sherman et al. |
| 2004/0197408 A1 | 10/2004 | Gravett |
| 2004/0201117 A1 | 10/2004 | Anderson |
| 2004/0202712 A1 | 10/2004 | Lambert et al. |
| 2004/0219214 A1 | 11/2004 | Gravett |
| 2004/0224001 A1 | 11/2004 | Pacetti et al. |
| 2004/0224003 A1 | 11/2004 | Schultz |
| 2004/0225077 A1 | 11/2004 | Gravett |
| 2004/0230176 A1 | 11/2004 | Shanahan et al. |
| 2004/0258662 A1 | 12/2004 | Gibbons, Jr. et al. |
| 2005/0025802 A1 | 2/2005 | Richard et al. |
| 2005/0038409 A1 | 2/2005 | Segal et al. |
| 2005/0049271 A1 | 3/2005 | Benjamin et al. |
| 2005/0054978 A1 | 3/2005 | Segal et al. |
| 2005/0055078 A1 | 3/2005 | Campbell |
| 2005/0080477 A1 | 4/2005 | Sydney et al. |
| 2005/0100580 A1 | 5/2005 | Osborne et al. |
| 2005/0101522 A1 | 5/2005 | Speck et al. |
| 2005/0123582 A1 | 6/2005 | Sung et al. |
| 2005/0152983 A1 | 7/2005 | Ashraf et al. |
| 2005/0159704 A1 | 7/2005 | Scott et al. |
| 2005/0171596 A1 | 8/2005 | Furst et al. |
| 2005/0182361 A1 | 8/2005 | Lennox |
| 2005/0186244 A1 | 8/2005 | Hunter et al. |
| 2005/0191323 A1 | 9/2005 | Chen |
| 2005/0191333 A1 | 9/2005 | Hsu |
| 2005/0209664 A1 | 9/2005 | Hunter et al. |
| 2005/0222191 A1 | 10/2005 | Falotico et al. |
| 2005/0234086 A1 | 10/2005 | Gu et al. |
| 2005/0234087 A1 | 10/2005 | Gu et al. |
| 2005/0234234 A1 | 10/2005 | Gu et al. |
| 2005/0238584 A1 | 10/2005 | Annapragada et al. |
| 2005/0239178 A1 | 10/2005 | Ruppen et al. |
| 2005/0250672 A9 | 11/2005 | Speck et al. |
| 2005/0251249 A1 | 11/2005 | Sahatjian et al. |
| 2005/0256564 A1 | 11/2005 | Yang et al. |
| 2005/0272758 A1 | 12/2005 | Bayever et al. |
| 2005/0278021 A1 | 12/2005 | Bates et al. |
| 2006/0020243 A1 | 1/2006 | Speck et al. |
| 2006/0020331 A1 | 1/2006 | Bates et al. |
| 2006/0040971 A1 | 2/2006 | Zhu et al. |
| 2006/0045901 A1 | 3/2006 | Weber et al. |
| 2006/0051392 A1 | 3/2006 | Heruth et al. |
| 2006/0052744 A1 | 3/2006 | Weber |
| 2006/0067977 A1* | 3/2006 | Labrecque et al. ........... 424/426 |
| 2006/0094745 A1 | 5/2006 | Ruffalo, Jr. |
| 2006/0112536 A1 | 6/2006 | Herweck et al. |
| 2006/0121117 A1 | 6/2006 | Hunter |
| 2006/0121545 A1 | 6/2006 | Molnar-Kimber et al. |
| 2006/0127445 A1 | 6/2006 | Hunter |
| 2006/0135549 A1 | 6/2006 | Graziani et al. |
| 2006/0135550 A1 | 6/2006 | Graziani et al. |
| 2006/0165753 A1 | 7/2006 | Richard |
| 2006/0183766 A1 | 8/2006 | Boni et al. |
| 2006/0184236 A1 | 8/2006 | Jones et al. |
| 2006/0188543 A1 | 8/2006 | Feng |
| 2006/0199834 A1 | 9/2006 | Zhu |
| 2006/0199954 A1 | 9/2006 | Shaw et al. |
| 2006/0224237 A1 | 10/2006 | Furst et al. |
| 2006/0230476 A1 | 10/2006 | Atanasoska et al. |
| 2006/0240113 A1 | 10/2006 | Hunter |
| 2006/0257444 A1 | 11/2006 | Tropsha et al. |
| 2006/0257445 A1 | 11/2006 | Tropsha et al. |
| 2006/0282114 A1 | 12/2006 | Barone |
| 2007/0003629 A1 | 1/2007 | Hunter |
| 2007/0003630 A1 | 1/2007 | Hunter |
| 2007/0020308 A1 | 1/2007 | Richard et al. |
| 2007/0020380 A1 | 1/2007 | Ding |
| 2007/0032694 A1 | 2/2007 | Dinkelborg et al. |
| 2007/0050010 A1 | 3/2007 | Bates et al. |
| 2007/0059434 A1 | 3/2007 | Roorda et al. |
| 2007/0065484 A1* | 3/2007 | Chudzik et al. ............... 424/426 |
| 2007/0073385 A1 | 3/2007 | Schaeffer et al. |
| 2007/0077347 A1 | 4/2007 | Richter |
| 2007/0078446 A1 | 4/2007 | Lavelle |
| 2007/0078513 A1 | 4/2007 | Campbell et al. |
| 2007/0117925 A1 | 5/2007 | Strickler et al. |
| 2007/0128118 A1 | 6/2007 | Yu et al. |
| 2007/0142772 A1 | 6/2007 | Deshmukh et al. |
| 2007/0142905 A1 | 6/2007 | Hezi-Yamit et al. |
| 2007/0150043 A1 | 6/2007 | Richter |
| 2007/0150047 A1 | 6/2007 | Ruane et al. |
| 2007/0161967 A1 | 7/2007 | Fischer, Jr. et al. |
| 2007/0162103 A1 | 7/2007 | Case et al. |
| 2007/0167735 A1 | 7/2007 | Zhong et al. |
| 2007/0168012 A1 | 7/2007 | Ragheb et al. |
| 2007/0184083 A1 | 8/2007 | Coughlin |
| 2007/0190103 A1 | 8/2007 | Hossainy et al. |
| 2007/0191934 A1 | 8/2007 | Blakstvedt et al. |
| 2007/0198080 A1 | 8/2007 | Ding et al. |
| 2007/0212386 A1 | 9/2007 | Patravale et al. |
| 2007/0212394 A1 | 9/2007 | Reyes et al. |
| 2007/0218246 A1 | 9/2007 | Ding |
| 2007/0219642 A1 | 9/2007 | Richter |
| 2007/0225799 A1 | 9/2007 | Doty |
| 2007/0237803 A1 | 10/2007 | Cheng et al. |
| 2007/0244284 A1 | 10/2007 | Cheng et al. |
| 2007/0244548 A1 | 10/2007 | Myers et al. |
| 2007/0264307 A1 | 11/2007 | Chen et al. |
| 2007/0265565 A1 | 11/2007 | Johnson |
| 2007/0276466 A1 | 11/2007 | Lavelle et al. |
| 2007/0282422 A1 | 12/2007 | Biggs et al. |

| | | | |
|---|---|---|---|
| 2007/0286814 A1 | 12/2007 | Sawant et al. |
| 2007/0298069 A1 | 12/2007 | Bucay-Couto et al. |
| 2008/0021385 A1 | 1/2008 | Barry et al. |
| 2008/0038307 A1 | 2/2008 | Hoffmann |
| 2008/0082552 A1 | 4/2008 | Krishnaswamy |
| 2008/0102033 A1 | 5/2008 | Speck et al. |
| 2008/0102034 A1 | 5/2008 | Speck et al. |
| 2008/0114331 A1* | 5/2008 | Holman et al. ............ 604/509 |
| 2008/0140002 A1 | 6/2008 | Ramzipoor et al. |
| 2008/0215137 A1 | 9/2008 | Epstein et al. |
| 2008/0255508 A1 | 10/2008 | Wang |
| 2008/0255509 A1 | 10/2008 | Wang |
| 2008/0255510 A1 | 10/2008 | Wang |
| 2008/0255658 A1 | 10/2008 | Cook et al. |
| 2008/0262412 A1 | 10/2008 | Atanasoska et al. |
| 2008/0274159 A1 | 11/2008 | Schultz |
| 2008/0274266 A1 | 11/2008 | Davis et al. |
| 2008/0276935 A1 | 11/2008 | Wang |
| 2008/0317827 A1 | 12/2008 | Wright et al. |
| 2009/0011116 A1 | 1/2009 | Herweck et al. |
| 2009/0047414 A1 | 2/2009 | Corbeil et al. |
| 2009/0069883 A1 | 3/2009 | Ding et al. |
| 2009/0076448 A1 | 3/2009 | Consigny et al. |
| 2009/0098176 A1 | 4/2009 | Helmus et al. |
| 2009/0105686 A1 | 4/2009 | Snow et al. |
| 2009/0105687 A1 | 4/2009 | Deckman et al. |
| 2009/0136560 A1 | 5/2009 | Bates et al. |
| 2009/0181937 A1 | 7/2009 | Faucher et al. |
| 2009/0182273 A1 | 7/2009 | Johnson |
| 2009/0187144 A1 | 7/2009 | Jayaraman |
| 2009/0208552 A1 | 8/2009 | Faucher et al. |
| 2009/0215882 A1 | 8/2009 | Bouzada et al. |
| 2009/0227948 A1 | 9/2009 | Chen et al. |
| 2009/0227949 A1 | 9/2009 | Knapp et al. |
| 2009/0238854 A1 | 9/2009 | Pacetti et al. |
| 2009/0246252 A1 | 10/2009 | Arps et al. |
| 2009/0324682 A1 | 12/2009 | Popowski |
| 2010/0030183 A1 | 2/2010 | Toner et al. |
| 2010/0055294 A1 | 3/2010 | Wang et al. |
| 2010/0063570 A1 | 3/2010 | Pacetti et al. |
| 2010/0068170 A1 | 3/2010 | Michal et al. |
| 2010/0069838 A1 | 3/2010 | Weber et al. |
| 2010/0069879 A1 | 3/2010 | Michal et al. |
| 2010/0081992 A1 | 4/2010 | Ehrenreich et al. |
| 2010/0087783 A1 | 4/2010 | Weber et al. |
| 2010/0198150 A1 | 8/2010 | Michal et al. |
| 2010/0198190 A1 | 8/2010 | Michal et al. |
| 2010/0272773 A1 | 10/2010 | Kangas et al. |
| 2010/0285085 A1 | 11/2010 | Stankus et al. |
| 2010/0324645 A1 | 12/2010 | Stankus et al. |
| 2010/0331816 A1 | 12/2010 | Dadino et al. |
| 2011/0054396 A1 | 3/2011 | Kangas et al. |
| 2011/0060275 A1 | 3/2011 | Christiansen |
| 2011/0129514 A1 | 6/2011 | Hossainy et al. |
| 2011/0137243 A1 | 6/2011 | Hossainy et al. |
| 2011/0143014 A1 | 6/2011 | Stankus et al. |
| 2011/0144577 A1 | 6/2011 | Stankus et al. |
| 2011/0144578 A1 | 6/2011 | Pacetti et al. |
| 2011/0152906 A1 | 6/2011 | Escudero et al. |
| 2011/0152907 A1 | 6/2011 | Escudero et al. |
| 2011/0178503 A1 | 7/2011 | Kangas |
| 2011/0190863 A1 | 8/2011 | Ostroot et al. |

FOREIGN PATENT DOCUMENTS

| | | | |
|---|---|---|---|
| EP | 0 702 557 A1 | 3/1996 |
| EP | 0 706 376 B2 | 4/1996 |
| EP | 0 711 158 A1 | 5/1996 |
| EP | 0 879 595 A2 | 11/1998 |
| EP | 1 118 325 A2 | 7/2001 |
| EP | 1 372 737 A2 | 1/2004 |
| EP | 1 468 660 A2 | 10/2004 |
| EP | 1 510 220 A1 | 3/2005 |
| EP | 1 539 266 A1 | 6/2005 |
| EP | 1 539 267 | 6/2005 |
| EP | 1 576 970 A1 | 9/2005 |
| EP | 1 586 338 A2 | 10/2005 |
| EP | 1 649 853 | 4/2006 |
| EP | 1 666 070 A1 | 6/2006 |
| EP | 1 666 071 B1 | 6/2006 |
| EP | 1 669 092 A1 | 6/2006 |
| EP | 1 857 127 | 11/2007 |
| EP | 1 913 962 A1 | 4/2008 |
| EP | 1 970 185 | 9/2008 |
| EP | 2 127 617 | 12/2009 |
| WO | WO 92/11890 A1 | 7/1992 |
| WO | WO 94/07484 | 4/1994 |
| WO | WO 94/07529 | 4/1994 |
| WO | WO 94/16706 | 8/1994 |
| WO | WO 94/26291 | 11/1994 |
| WO | WO 95/03036 | 2/1995 |
| WO | WO 95/03795 | 2/1995 |
| WO | WO 96/25176 | 8/1996 |
| WO | WO 96/39949 | 12/1996 |
| WO | WO 97/25977 | 7/1997 |
| WO | WO 98/02114 | 1/1998 |
| WO | WO 98/14174 | 4/1998 |
| WO | WO 98/30249 | 7/1998 |
| WO | WO 98/36784 | 8/1998 |
| WO | WO 98/57671 A2 | 12/1998 |
| WO | WO 99/08729 | 2/1999 |
| WO | WO 00/21584 | 4/2000 |
| WO | WO 00/32238 | 6/2000 |
| WO | WO 00/32267 | 6/2000 |
| WO | WO 00/44414 | 8/2000 |
| WO | WO 00/45744 A1 | 8/2000 |
| WO | WO 01/24866 | 4/2001 |
| WO | WO 02/076509 A2 | 10/2002 |
| WO | WO 2004/006976 | 1/2004 |
| WO | WO 2004/026357 A1 | 4/2004 |
| WO | WO 2004/028582 A2 | 4/2004 |
| WO | WO 2004/028610 | 4/2004 |
| WO | WO 2005/011769 A2 | 2/2005 |
| WO | WO 2006/023859 A1 | 3/2006 |
| WO | WO 2006/081210 A2 | 8/2006 |
| WO | WO 2006/101573 A1 | 9/2006 |
| WO | WO 2006/124647 A1 | 11/2006 |
| WO | WO 2007/047416 A2 | 4/2007 |
| WO | WO 2007/079560 A2 | 7/2007 |
| WO | WO 2007/134239 A2 | 11/2007 |
| WO | WO 2007/139931 A2 | 12/2007 |
| WO | WO 2007/149161 A2 | 12/2007 |
| WO | WO 2008/003298 A2 | 1/2008 |
| WO | WO 2008/063576 A2 | 5/2008 |
| WO | WO 2008/086794 | 7/2008 |
| WO | WO 2008/114585 | 9/2008 |

OTHER PUBLICATIONS

European Search Report for EP 09160605, Jul. 20, 2009.
European Search Report for EP 10168411, Nov. 30, 2010.
European Search Report for EP 10168412, Nov. 30, 2010.
European Search Report for EP 10189393, Apr. 4, 2011.
International Search Report for International Application No. PCT/US2010/028599, dated Dec. 21, 2010.
Office Action in U.S. Appl. No. 11/942,459, dated Jul. 19, 2011.
Office Action in U.S. Appl. No. 12/121,986, dated Jul. 7, 2011.
Office Action in U.S. Appl. No. 12/123,951, dated Jun. 16, 2011.
Office Action in U.S. Appl. No. 12/123,956, dated Jun. 28, 2011.
Office Action in U.S. Appl. No. 12/135,648, dated Feb. 18, 2011.
Office Action in U.S. Appl. No. 12/135,648, dated Jul. 13, 2011.
Office Action in U.S. Appl. No. 12/731,835, dated Jul. 6, 2011.
Office Action in U.S. Appl. No. 13/042,213, dated Jul. 8, 2011.
Rowinsky, E. K., et al., "Drug therapy: paclitaxel (taxol)", Review Article, N Engl J Med, vol. 332, No. 15, pp. 1004-1014, (1995).
Baumbach et al., "Local Drug Delivery: Impact of Pressure Substance Characteristics, and Stenting on Drug Transfer Into the Arterial Wall," Catheterization and Cardiovascular Interventions, vol. 47, pp. 102-106 (1999).
Charles et al., "Ceramide-Coated Balloon Catheters Limit Neointimal Hyperplasia after Stretch Injury in Carotid Arteries;" Circulation Research 2000; 87:282-288.
Chun Li, et al, "Synthesis, Biodistribution and Imaging Properties of Indium-111-DTPA-Paclitaxel in Mice Bearing Mammary Tumors." The Journal of Nuclear Medicine, vol. 38, No. 7, Jul. 1997, 1042-1047.
Creel et al., 2000 Circulation Research. Bd. 86, S. 879-884.

D. M. Long et al., "Perflurocarbon Compounds as X-Ray Contrast Media in the Lungs." Bulletin de la Societe Internationale De Chirurgie, vol. 2, 1975, 137-141.

D.M. Jackson et al., "Current usage of contract agents, anticoagulant and antiplatelet drugs in angiography and angioplasty in the UK," Department of Diagnostic Radiology, Hammersmith Hospital, London, UK, Clinical Radiology (1995), 50, pp. 699-704.

English Language Abstract for DE 101 15 740.
English Language Abstract for EP 1 372 737 A2.
English Language Abstract for EP 1 539 266 A1.
English Language Abstract for EP 1 539 267.
English Language Abstract for EP 1 666 070 A1.
English Language Abstract for EP 1 666 071 A1.
English Language Abstract for EP 1 669 092 A1.
English Language Abstract for EP 1 857 127.
English Language Abstract for WO 02/076509.
English Language Abstract for WO 2004/028582.
English Language Abstract for WO 2004/028610.
English Language Abstract for WO 2008/003298 A2.
English Language Abstract for WO 2008/086794.

Gyula Ostoros et al., "Fatal Pulmonary Fibrosis Induced Paclitaxel: A Case Report and Review of the Literature." International Journal of Gynecological Cancer, vol. 16, Suppl. 1, Jan. 2006, at pp. 391-393.

Gyula Ostoros et al., "Paclitaxel Induced Pulmonary Fibrosis," Lung Cancer, Elsevier, Amsterdam, NL, vol. 41, Aug. 1, 2003, at p. S280.

Herdeg et al., "Paclitaxel: Ein Chemotherapeuticum zum Restenoseprophylaxe? Experimentell Untersuchungen in vitro and in vivo." Z Kardiol, vol. 89 (2000) pp. 390-397.

Hershberger et al., "Calcitriol (1, 25-dihydroxy cholecalciferol) Enhances Paclitaxel Antitumor Activity in Vitro and in Vivo and Accelerates Paclitaxel-Induced Apoptosis." Clin. Can. Res. 7: 1043-1051 (Apr. 2001).

International Search Report for International Application No. PCT/US2008/006348, dated Jan. 28, 2009.

International Search Report for International Application No. PCT/US2008/006348, dated Nov. 26, 2008.

International Search Report for International Application No. PCT/US2008/006415, dated Nov. 24, 2008.

International Search Report for International Application No. PCT/2007/024108, dated Aug. 7, 2008.

International Search Report for International Application No. PCT/2007/024108, Nov. 20, 2008.

International Search Report for International Application No. PCT/2008/006417, Nov. 24, 2008.

International Search Report for International Application No. PCT/2008/007177, Dec. 2, 2008.

International Search Report for International Application No. PCT/2008/007177, Sep. 16, 2008.

International Search Report for International Application No. PCT/2009/004868, Jan. 1, 2010.

International Search Report for International Application No. PCT/2009/004868, May 21, 2010.

International Search Report for International Application No. PCT/US2007/024116, dated Nov. 20, 2008.

J.F. Mitchel et al., "Inhibition of Platelet Deposition and Lysis of Intracoronary Thrombus During Balloon Angioplasty Using Urokinase-Coated Hydrogel Balloons." Circulation 90, (Oct. 1994), pp. 1979-1988.

J.H. Baron, et al., "In vitro evaluation of c7E3-Fab (ReoPro) eluting polymer-coated coronary stents." Cardiovascular Research, 46 (2000) pp. 585-594.

Journal of Microencapsulation, 17, 6, Nov. 2, 2000, p. 789-799.

K. Kandarpa et al., "Mural Delivery of Iloprost with Use of Hydrogel-coated Balloon Catheters Suppresses Local Platelet Aggregation." J. Vasc. Interv. Radiol. 8, pp. 997-1004, Nov./Dec. 1997.

K. Kandarpa et al., "Site-specific Delivery of Iloprost during Experimental Angioplasty Suppresses Smooth Muscle Cell Proliferation." J. Vasc. Interv. Radiol. 9, pp. 487-493, (1998).

Ken Iwai, et al., "Use of oily contrast medium for selective drug targeting to sumor: Enhanced therapeutic effect and X-ray image," Cancer Research, 44, 2115-2121, May 1994.

Laure Champion et al., "Brief Communication: Sirolimus-Associated Pneumonitis: 24 Cases in Renal Transplant Recipients." Annals of Internal Medicine, vol. 144, No. 7, Apr. 4, 2006, at pp. 505-509.

Leo, et al., (1971). "Partition coefficients and their uses." Chem Rev 71 (6):525-537.

Li J. Chiang et al., "Potent inhibition of tumor survival in vivo by β-lapachone plus taxol: Combining drugs imposes different artificial checkpoints." PNAS, vol. 96, No. 23, Nov. 9, 1999, at pp. 13369-13374.

New England Journal of Medicine, 1995, 332: 1004-1014.

Office Action in co-pending U.S. Appl. No. 11/942,452, dated Apr. 29, 2010.

Office Action in co-pending U.S. Appl. No. 11/942,452, dated Oct. 13, 2010.

Office Action in co-pending U.S. Appl. No. 11/942,459, dated Apr. 20, 2010.

Office Action in co-pending U.S. Appl. No. 11/942,459, dated Sep. 27, 2010.

PPD, "Evaluation of Butanol-Buffer Distribution Properties of C6-Ceraminde." PPD Project No. 7557-001, Aug. 20, 2008, pp. 1-14.

Prashant N. Chhajed et al., "Patterns of Pulmonary Complications Associated with Sirolimus." Respiration: International Review of Thoracic Diseases, vol. 73, No. 3, Mar. 2006, at pp. 367-374.

Sangster, James (1997). "Octanol-Water Partition Coefficients: Fundamentals and Physical Chemistry." vol. 2 of Wioley Series in Solution Chemistry. Chichester: John Wiley & Sons Ltd.

Scheller et al., Paclitaxel Balloon Coating, a Novel Method for Prevention and Therapy of Restenosis. Circulation 2004; 110;810-814; originally published online Aug. 9, 2004.

Seymour R. Halpin SF et al., "Corticosteroid prophylaxis for patients with increased risk of adverse reactions to intravascular contrast agents: a survey of current practice in the UK." Department of Radiology, University Hospital of Wales, Heath Park, Cardiff, Clinical Radiology (1994), 49, pp. 791-795.

Toshimitsu Konno, M.D., et al., "Selective targeting of anti-cancer drug and simultaneous imaging enhancement in solid tumors by arterially administered lipid contrast medium." Cancer 54:2367-2374, 1984.

Yushmanov, et al., J. Colloid Interface Sci., 1997; 191(2):384-90.

* cited by examiner

DRUG RELEASING COATINGS FOR MEDICAL DEVICES

CROSS REFERENCE TO RELATED APPLICATIONS

This is a divisional of application Ser. No. 11/942,452, filed Nov. 19, 2007, which application claims the benefit of priority under 35 U.S.C. §119 of U.S. Provisional Application No. 60/860,084, filed on Nov. 20, 2006, U.S. Provisional Application No. 60/880,742, filed Jan. 17, 2007, U.S. Provisional Application No. 60/897,427, filed on Jan. 25, 2007, U.S. Provisional Application No. 60/903,529 filed on Feb. 26, 2007, U.S. Provisional Application No. 60/926,850 filed Apr. 30, 2007, U.S. Provisional Application No. 60/904,473 filed Mar. 2, 2007, U.S. Provisional Application No. 60/981,380 filed Oct. 19, 2007, and U.S. Provisional Application 60/981, 384 filed Oct. 19, 2007, the disclosures of all of which are incorporated by reference herein.

FIELD OF THE INVENTION

Embodiments of the present invention relate to coated medical devices, and particularly to coated balloon catheters, and their use for rapidly delivering a therapeutic agent to particular tissue or body lumen. Embodiments of the present invention also relate to methods of manufacturing these medical devices, the coatings provided on these medical devices, the solutions for making those coatings, and methods for treating a body lumen such as the vasculature, including particularly arterial vasculature, for example, using these coated medical devices.

BACKGROUND OF THE INVENTION

It has become increasingly common to treat a variety of medical conditions by introducing a medical device into the vascular system or other lumen within a human or veterinary patient such as the esophagus, trachea, colon, biliary tract, or urinary tract. For example, medical devices used for the treatment of vascular disease include stents, catheters, balloon catheters, guide wires, cannulas and the like. While these medical devices initially appear successful, the benefits are often compromised by the occurrence of complications, such as late thrombosis, or recurrence of disease, such as stenosis (restenosis), after such treatment.

Restenosis, for example, involves a physiological response to the vascular injury caused by angioplasty. Over time, de-endotheliaziation and injury to smooth muscle cells results in thrombus deposition, leukocyte and macrophage infiltration, smooth muscle cell proliferation/migration, fibrosis and extracellular matrix deposition. Inflammation plays a pivotal role linking early vascular injury to the eventual consequence of neointimal growth and lumen compromise. In balloon-injured arteries, leukocyte recruitment is confined to early neutrophil infiltration, while in stented arteries, early neutrophil recruitment is followed by prolonged macrophage accumulation. The widespread use of coronary stents has altered the vascular response to injury by causing a more intense and prolonged inflammatory state, due to chronic irritation from the implanted foreign body, and in the case of drug eluting stents (DES), from insufficient biocompatibility of the polymer coating.

Over the past several years, numerous local drug delivery systems have been developed for the treatment and/or the prevention of restenosis after balloon angioplasty or stenting. Examples include local drug delivery catheters, delivery balloon catheters, and polymeric drug coated stents. Given that many diseases affect a specific local site or organ within the body, it is advantageous to preferentially treat only the affected area. This avoids high systemic drug levels, which may result in adverse side effects, and concentrates therapeutic agents in the local area where they are needed. By treating just the diseased tissue, the total quantity of drug used may be significantly reduced. Moreover, local drug delivery may allow for the use of certain effective therapeutic agents, which have previously been considered too toxic or non-specific to use systemically.

One example of a local delivery system is a drug eluting stent (DES). The stent is coated with a polymer into which drug is impregnated. When the stent is inserted into a blood vessel, the polymer degrades and the drug is slowly released. The slow release of the drug, which takes place over a period of weeks to months, has been reported as one of the main advantages of using DES. However, while slow release may be advantageous in the case where a foreign body, such as a stent, is deployed, which is a source of chronic irritation and inflammation, if a foreign body is not implanted it is instead advantageous to rapidly deliver drug to the vascular tissue at the time of treatment to inhibit inflammation and cellular proliferation following acute injury. Thus, a considerable disadvantage of a DES, or any other implanted medical device designed for sustained release of a drug, is that the drug is incapable of being rapidly released into the vessel.

Additionally, while drug-eluting stents were initially shown to be an effective technique for reducing and preventing restenosis, recently their efficacy and safety have been questioned. A life-threatening complication of the technology, late thrombosis, has emerged as a major concern. Drug eluting stents cause substantial impairment of arterial healing, characterized by a lack of complete re-endothelialization and a persistence of fibrin when compared to bare metal stents (BMS), which is understood to be the underlying the cause of late DES thrombosis. Concerns have also been raised that the polymeric matrix on the stent in which the anti-proliferative drug is embedded might exacerbate inflammation and thrombosis, since the polymers used are not sufficiently biocompatible. These polymeric systems are designed to facilitate long-term sustained release of drug over a period of days, months, or years, not over a period of seconds or minutes. Rapid release of drug, an intent of embodiments of the present invention, from these polymeric systems is not possible. Thus, combining a therapeutic agent with a polymer in a medical device coating may have significant disadvantages.

Another important limitation of the DES is that the water insoluble drugs are not evenly distributed in the polymeric matrix of the coating. Furthermore, drug and polymer are concentrated on the struts of the stent, but not in gaps between the struts. The non-uniform distribution of drug causes non-uniform drug release to the tissue of the vessel walls. This may cause tissue damage and thrombosis in areas exposed to excess drug and hyperplasia and restenosis areas that are undertreated. Thus, there is a need to improve the uniformity of drug delivery to target tissues by improving drug solubility in coatings of medical devices by increasing the drug's compatibility with carriers in the coatings, such as a polymeric matrix, thereby eliminating or reducing the size of drug crystal particles in the polymeric matrix or other coating to create a uniform drug distribution in the drug coating on the medical device.

Yet another important limitation of the DES is that only a limited amount of an active agent can be loaded into the relatively small surface area of the stent.

Non-stent based local delivery systems, such as balloon catheters, have also been effective in the treatment and prevention of restenosis. The balloon is coated with an active agent, and when the blood vessel is dilated, the balloon is pressed against the vessel wall to deliver the active agent. Thus, when balloon catheters are used, it is advantageous for the drug in the coating to be rapidly released and absorbed by blood vessel tissues. Any component of the coating that inhibits rapid release, such as a lipid or polymer or an encapsulating particle, is necessarily disadvantageous to the intended use of the balloon catheter, which is inflated for a very brief period of time and then removed from the body.

Hydrophilic drugs, such as heparin, have been reported to be deliverable by polymeric hydrogel coated balloon catheters. However, a polymeric hydrogel coating can not effectively deliver water insoluble drugs (such as paclitaxel and rapamycin), because they can not mix with the hydrogel coating.

The iodine contrast agent iopromide has been used with paclitaxel to coat balloon catheters and has some success in treatment of restenosis. It was reported that contrast agent improves adhesion of paclitaxel to the balloon surface. Iodinated contrast agents suffer from several well known disadvantages. When used for diagnostic procedures, they may have complication rates of 5-30%. These agents are associated with the risk of bradycardia, ventricular arrthymia, hypotension, heart block, sinus arrest, sinus tachycardia, and fibrillation. Iodine contrast agents may also induce renal failure, and as a result there are significant efforts to remove these contrast agents from the vascular system after diagnostic procedures.

Iodinated X-ray contrast agents are large hydrophilic spherical molecules. They are characterized by an extracellular distribution and rapid glomerular filtration and renal excretion. They are unable to cross membrane lipid bilayers to enter cells of the vasculature because they are large, polar, hydrophilic molecules. They are therefore not optimally effective at carrying hydrophobic drugs such as paclitaxel into cells, and the percent of paclitaxel reported to be taken up by vascular tissue after deployment of these devices is only 5-20%.

Alternatively, balloon catheters are reported to have been coated with hydrophobic therapeutic agents that have been mixed with oils or lipids or encapsulated in particles such as liposomes or polymers. All of these drug delivery formulations have significant disadvantages. Unlike hydrophilic contrast agents, oils and lipids mix well with water-insoluble drugs such as paclitaxel or rapamycin, but the particle sizes of oils used for solubilizing the therapeutic agents are relatively unstable, ranging in a broad particle size distribution from several hundred nanometers to several microns in diameter.

Loading capacity of conventional micelles is low. Another disadvantage of oil-based liposome formulations is the dependence of drug absorption on the rate and extent of lipolysis. Lipolysis of oil-based triglycerides is difficult and dependent upon many factors, and triglycerides must be digested and drug released in order to be absorbed by diseased tissue. The amount of hydrophobic drug delivered to tissues by these agents will be low, because liposomes and micelles cannot efficiently release hydrophobic drug, which they carry away before it can be absorbed by tissues. Oils and lipids are therefore not effective at rapidly and efficiently facilitating tissue uptake of drug during a very brief device deployment time, and no report has shown these types of coatings to be effective.

Drug that is encapsulated in polymeric particles may take even longer to diffuse from the coating and will have further difficulty permeating target tissues rapidly. Microspheres formed with polymeric materials, such as polyesters, when used to encapsulate water insoluble drugs, are unable to release the drug until the polymeric material is degraded. Thus, these polymeric microspheres are useful for sustained release of drug over a long period of time but cannot rapidly release drug and facilitate tissue uptake.

Combining drugs and medical devices is a complicated area of technology. It involves the usual formulation challenges, such as those of oral or injectable pharmaceuticals, together with the added challenge of maintaining drug adherence to the medical device until it reaches the target site and subsequently delivering the drug to the target tissues with the desired release and absorption kinetics. Drug coatings of medical devices must also have properties such that they do not crack upon expansion and contraction of the device, for example, of a balloon catheter or a stent. Furthermore, coatings must not impair functional performance such as burst pressure and compliance of balloons or the radial strength of self- or balloon-expanded stents. The coating thickness must also be kept to a minimum, since a thick coating would increase the medical device's profile and lead to poor trackability and deliverability. These coatings generally contain almost no liquid chemicals, which typically are often used to stabilize drugs. Thus, formulations that are effective with pills or injectables might not work at all with coatings of medical device. If the drug releases from the device too easily, it may be lost during device delivery before it can be deployed at the target site. If the drug adheres too strongly, the device may be withdrawn before the drug can be released and absorbed by tissues at the target tissues.

Thus, there is still a need to develop highly specialized coatings for medical devices that can rapidly deliver therapeutic agents, drugs, or bioactive materials directly into a localized tissue area during or following a medical procedure, so as to treat or prevent vascular and nonvascular diseases such as restenosis. The device should quickly release the therapeutic agent in an effective and efficient manner at the desired target location, where the therapeutic agent should rapidly permeate the target tissue.

SUMMARY OF THE INVENTION

The present inventor has found that coating the exterior surface of a medical device, and particularly of a balloon catheter or a stent, for example, with a layer comprising a therapeutic agent and an additive that has both a hydrophilic part and a hydrophobic part is useful in solving the problems associated with the coatings discussed above. Surprisingly, the present inventor has found that the at least one additive according to embodiments of the present invention, which comprises a hydrophilic part and a hydrophobic part, in combination with a therapeutic agent, forms an effective drug delivery coating on a medical device without the use of oils and lipids, thereby avoiding the lipolysis dependence and other disadvantages of conventional oil-based coating formulations. Moreover, the additives according to embodiments of the present invention facilitate rapid drug elution and superior permeation of drug into tissues at a disease site. Thus, coatings according to embodiments of the present invention provide an enhanced rate and/or extent of absorption of the hydrophobic therapeutic agent in diseased tissues of the vasculature or other body lumen.

In one embodiment, the present invention relates to a medical device for delivering a therapeutic agent to a tissue, the device comprising a layer overlying an exterior surface of the medical device. The device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve. Further, the tissue includes tissue of one of coronary vasculature, peripheral vasculature, cerebral vasculature, esophagus, airways, sinus, trachea, colon, biliary tract, urinary tract, prostate, and brain passages.

In one embodiment of the medical device, the layer overlying the exterior surface of the medical device comprises a therapeutic agent and an additive, wherein the additive comprises a hydrophilic part and a hydrophobic part, wherein the therapeutic agent is not enclosed in micelles or encapsulated in polymer particles, and wherein the layer does not include an iodine covalent bonded contrast agent. In one embodiment, the layer overlying the exterior surface of the medical device consists essentially of the therapeutic agent and the additive.

In one embodiment, the layer overlying the exterior surface of the medical device does not include oil, a lipid, or a polymer. In another embodiment, the layer overlying the exterior surface of the medical device does not include oil. In another embodiment, the layer overlying the exterior surface of the medical device does not include a polymer. In another embodiment, the layer overlying the exterior surface of the medical device does not include a purely hydrophobic additive. In another embodiment, the layer overlying the exterior surface of the medical device does not include a dye. In another embodiment, the layer overlying the exterior surface of the medical device does not include salicylic acid or salts thereof. In yet another this embodiment, the layer overlying the exterior surface of the medical device does not include sodium salicylate.

In one embodiment, the additive in the layer comprising the therapeutic agent and the additive is an ionic or non-ionic surfactant. In another embodiment, the additive is a vitamin or derivative thereof. In another embodiment, the additive is an amino acid or derivative thereof. In another embodiment, the additive is a protein or derivative thereof. In another embodiment, the additive is an albumin. In another embodiment, the additive is soluble in an aqueous solvent and is soluble in an organic solvent. In another embodiment, the additive is an organic acid or an anhydride thereof. In yet another embodiment, the additive is chosen from sorbitan oleate and sorbitan fatty esters.

In one embodiment, the additive in the layer comprising the therapeutic agent and the additive is chosen from PEG fatty esters and alcohols, glycerol fatty esters, sorbitan fatty esters, PEG glyceryl fatty esters, PEG sorbitan fatty esters, sugar fatty esters, PEG sugar esters, vitamins and derivatives, amino acids, multi amino acids and derivatives, peptides, polypeptides, proteins, quaternary ammonium salts, organic acids, salts and anhydrides. In another embodiment, the additive in the layer comprising the therapeutic agent and the additive is chosen from chemical compounds having multiple hydroxyl, amino, carbonyl, carboxyl, or ester moieties.

In another embodiment, the additive in the layer comprising the therapeutic agent and the additive is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polylyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases (proteins), benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), L-ascorbic acid and its salt, D-glucoascorbic acid and its salt, tromethamine, glucamine, glucoheptonic acid, glucomic acid, gluconolactone, glucosamine, glutamic acid (chemical compounds with multiple hydroxyl, amino, carbonyl, carboxyl, or ester moieties).

In another embodiment, the additive in the layer comprising the therapeutic agent and the additive is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly(glycidol), Octyl-betha-D-glycopyranoside, and deconoyl-N-methylglucamide.

In another embodiment, the additive in the layer comprising the therapeutic agent and the additive is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the therapeutic agent in the layer comprising the therapeutic agent and the additive is one of paclitaxel and analogues thereof, rapamycin and analogues thereof, beta-lapachone and analogues thereof, biological vitamin D and analogues thereof, and a mixture of these therapeutic agents. In another embodiment, the therapeutic agent is in combination with a second therapeutic agent, wherein the therapeutic agent is one of paclitaxel, rapamycin, and analogues thereof, and wherein the second therapeutic agent is one of beta-lapachone, biological active vitamin D and their analogues. In one embodiment, the therapeutic agent is not water soluble.

In one embodiment, the additive enhances penetration and absorption of the therapeutic agent in tissue. In another embodiment, the additive penetrates tissue, and the therapeutic agent is not water soluble. In another embodiment, the additive has a water and ethanol solubility of at least 1 mg/ml and the therapeutic agent is not water soluble.

In one embodiment, the concentration of the additive in the layer is from 1 to 10 µg/mm$^2$. In one embodiment, the concentration of the therapeutic agent in the layer is from 1 to 20 µg/mm². In another embodiment, the concentration of the therapeutic agent in the layer is from 2 to 6 µg/mm².

In one embodiment of the medical device, the device is capable of delivering the therapeutic agent to the tissue in about 0.2 to 2 minutes. In another embodiment, the device is capable of delivering the therapeutic agent to the tissue in about 0.1 to 1 minute.

In one embodiment, the medical device comprising a layer overlying an exterior surface of the medical device further comprises an adherent layer between the exterior surface of the medical device and the layer. In another embodiment, the device further comprises a top layer overlying the surface of the layer to prevent loss of drug during transit through a body to the tissue. In another embodiment, the medical device further comprises a dimethylsulfoxide solvent layer, wherein the dimethylsulfoxide solvent layer is overlying the surface of the layer.

In another embodiment of the medical device, the layer overlying the exterior surface of the medical device comprises a therapeutic agent and at least two additives, wherein each of the additives comprises a hydrophilic part and a hydrophobic part and wherein each additive is soluble in polar organic solvent and is soluble in water, and wherein the therapeutic agent is not enclosed in micelles or encapsulated in polymer particles. In one aspect of this embodiment, the polar organic solvent is selected from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water.

In another embodiment of the medical device, the layer overlying the exterior surface of the medical device comprises a therapeutic agent and an additive, wherein the additive comprises a hydrophilic part and a hydrophobic part, wherein the additive reduces crystal size and number of particles of the therapeutic agent, and wherein the therapeutic agent is not water soluble and is not enclosed in micelles or encapsulated in polymer particles.

In another embodiment of the medical device, the layer overlying the exterior surface of the medical device comprises a therapeutic agent and an additive, wherein the additive comprises a hydrophilic part and a hydrophobic part, wherein the additive has a fatty chain of an acid, ester, ether, or alcohol, wherein the fatty chain directly inserts into lipid membrane structures of tissue, wherein the therapeutic agent is not water soluble and is not enclosed in micelles or encapsulated in polymer particles, and wherein the layer does not include an iodine covalent bonded contrast agent.

In another embodiment of the medical device, the layer overlying the exterior surface of the medical device comprises a therapeutic agent and an additive, wherein the additive comprises a hydrophilic part and a hydrophobic part, wherein the additive penetrates into and rearranges lipid membrane structures of the tissue, and wherein the therapeutic agent is not water soluble and is not enclosed in micelles or encapsulated in polymer particles.

In another embodiment of the medical device, the layer overlying the exterior surface of the medical device comprises a therapeutic agent and an additive, wherein the additive comprises a hydrophilic part and a hydrophobic part, wherein the additive is a surfactant and has a fatty chain of an acid, ester, ether, or alcohol, wherein the fatty chain directly inserts into the lipid membrane structures of the tissue, wherein the therapeutic agent is not water soluble and is not enclosed in micelles or encapsulated in polymer particles, and wherein the layer does not include an iodine covalent bonded contrast agent.

In another embodiment of the medical device, the layer overlying the exterior surface of the medical device comprises a therapeutic agent and an additive, wherein the additive comprises a hydrophilic part and a hydrophobic part, wherein the additive has more than four hydroxyl, carboxyl, or amine groups as components of the hydrophilic part, wherein the therapeutic agent is not water soluble and is not enclosed in micelles or encapsulated in polymer particles, and wherein the layer does not include an iodine covalent bonded contrast agent.

In yet another embodiment, the present invention relates to a stent coating for delivering a therapeutic agent to a tissue, the stent coating comprising a layer overlying a surface of the stent. In one aspect of this embodiment, the layer overlying the surface of the stent comprises a therapeutic agent, an additive, and a polymer matrix, wherein the therapeutic agent is dispersed, but not encapsulated, as particles in the polymer matrix, wherein the additive comprises a hydrophilic part and a hydrophobic part, wherein the additive improves the compatibility of the therapeutic agent and the polymer matrix, and wherein the additive reduces the particle sizes and improves uniformity of distribution of the therapeutic agent in the polymer matrix.

In yet another embodiment, the present invention relates to a medical device for delivering a drug to a tissue that is prepared from a mixture. In one aspect of this embodiment, the mixture comprises an organic phase containing drug particles dispersed therein and an aqueous phase containing a water soluble additive, wherein the additive is not an iodine covalent bonded contrast agent or a dye. In another aspect of this embodiment, the preparation mixture includes homogenization under high shear conditions and optionally under pressure. In another aspect of this embodiment, the water soluble additive is selected from albumin, polyethylene glycol, polyvinyl alcohol, polyvinylpyrrolidinone, polypeptides, water soluble surfactants, water soluble vitamins, and proteins.

In another embodiment, the present invention relates to a balloon catheter for delivering a therapeutic agent to a blood vessel, the catheter comprising a coating layer overlying an exterior surface of a balloon. In one embodiment of the balloon catheter, the coating layer comprises a therapeutic agent and an additive, wherein the additive comprises a hydrophilic part and a hydrophobic part, and wherein the therapeutic agent is not enclosed in micelles or encapsulated in polymer particles, and wherein the layer does not include an iodine covalent bonded contrast agent. In one aspect of this embodiment, the coating layer overlying an exterior surface of the exterior surface of the medical device consists essentially of the therapeutic agent and the additive.

In one embodiment of the balloon catheter, the additive in the coating layer is an ionic or non-ionic surfactant. In another embodiment, the additive is a vitamin or derivative thereof. In another embodiment, the additive is an amino acid or derivative thereof. In another embodiment, the additive is a protein or derivative thereof. In another embodiment, the additive is a albumin. In another embodiment, the additive is soluble in an aqueous solvent and is soluble in an organic solvent. In another embodiment, the additive is an organic acid or an anhydride thereof. In yet another embodiment, the additive is chosen from sorbitan oleate and sorbitan fatty esters.

In one embodiment of the balloon catheter, the coating layer overlying the exterior surface of the balloon does not include a purely hydrophobic additive. In another embodiment, the coating layer overlying the exterior surface of the balloon does not contain a dye. In another embodiment, the coating layer overlying the exterior surface of the balloon does not include salicylic acid or salts thereof. In another embodiment, the coating layer overlying the surface of the balloon does not include sodium salicylate. In another embodiment, the coating layer overlying the surface of the balloon does not include oil, a lipid, or a polymer. In yet another embodiment, the coating layer overlying the surface of the balloon does not include oil. In another aspect of this embodiment, the coating layer does not include a polymer.

In one embodiment, the additive in the coating layer comprising the therapeutic agent and the additive is chosen from PEG fatty esters and alcohols, glycerol fatty esters, sorbitan fatty esters, PEG glyceryl fatty esters, PEG sorbitan fatty esters, sugar fatty esters, PEG sugar esters, vitamins and derivatives, amino acids, multi amino acids and derivatives, peptides, polypeptides, proteins, quaternary ammonium salts, organic acids, salts and anhydrides.

In another embodiment, the additive in the coating layer comprising the therapeutic agent and the additive is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases (proteins), benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), L-ascorbic acid and its salt, D-glucoascorbic acid and its salt, tromethamine, glucamine, glucoheptonic acid, glucomic acid, gluconolactone, glucosamine, glutamic acid (chemical compounds with multiple hydroxyl, amino, carbonyl, carboxyl, or ester moieties).

In another embodiment, the additive in the coating layer comprising the therapeutic agent and the additive is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly (glycidol), Octyl-betha-D-glycopyranoside, and deconoyl-N-methylglucamide.

In another embodiment, the additive in the coating layer comprising the therapeutic agent and the additive is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the therapeutic agent is one of paclitaxel and analogues thereof, rapamycin and analogues thereof, beta-lapachone and analogues thereof, biological vitamin D and analogues thereof, and a mixture of these therapeutic agents. In another embodiment, the therapeutic agent is in combination with a second therapeutic agent, wherein the therapeutic agent is one of paclitaxel, rapamycin, and analogues thereof, and wherein the second therapeutic agent is one of beta-lapachone, biological active vitamin D and their analogues. In one embodiment, the therapeutic agent is not water soluble.

In one embodiment, the additive enhances penetration and absorption of the therapeutic agent in the blood vessel. In another embodiment, the additive penetrates the blood vessel, and the therapeutic agent is not water soluble. In another embodiment, the additive has a water and ethanol solubility of at least 1 mg/ml, and the therapeutic agent is not water soluble.

In one embodiment of the balloon catheter, the catheter further comprises an adherent layer between the exterior surface of the balloon and the coating layer. In another embodiment, the catheter further comprises a top layer overlying the coating layer, wherein the top layer prevents loss of the therapeutic agent during transit through a body to the blood vessel. In another embodiment, the catheter further comprises a dimethylsulfoxide solvent layer, wherein the dimethylsulfoxide solvent layer is overlying the surface of the coating layer.

In one embodiment, the balloon catheter is capable of delivering the therapeutic agent to the blood vessel in about 0.2 to 2 minutes. In another embodiment, the balloon catheter is capable of delivering the therapeutic agent to the blood vessel in about 0.1 to 1 minute.

In one embodiment of the balloon catheter, the concentration of the therapeutic agent in the coating layer is from 1 to 20 μg/mm$^2$. In another embodiment, the concentration of the therapeutic agent in the coating layer is from 2 to 6 μg/mm$^2$. In one embodiment, the concentration of the additive in the coating layer is from 1 to 10 μg/mm$^2$.

In yet a further embodiment, the present invention relates to a balloon catheter for delivering a therapeutic agent to a blood vessel. In one aspect of this embodiment, the catheter comprises an elongate member having a lumen and a distal end, an expandable balloon attached to the distal end of the elongate member and in fluid communication with the lumen, and a coating layer overlying an exterior surface of the balloon. In one aspect of this embodiment, the coating layer overlying the surface of the balloon comprises a therapeutic agent and an additive, wherein the additive comprises a hydrophilic part and a hydrophobic part, wherein the therapeutic agent is not enclosed in micelles or encapsulated in particles or delayed release carriers, wherein the layer does not include oil, a lipid, a polymer, or an iodine covalent bonded contrast agent, and wherein the catheter is capable of delivering the therapeutic agent to the blood vessel in less than about 2 minutes. In one aspect of this embodiment, the layer does not include a purely hydrophobic additive. In another aspect of this embodiment, the layer does not contain a dye. In yet another aspect of this embodiment, the additive is a polypeptide or protein.

In one embodiment, the coating layer overlying the surface of the balloon consists essentially of the therapeutic agent and the additive.

In one embodiment, the therapeutic agent in the coating layer overlying the surface of the balloon is paclitaxel and analogues thereof. In another embodiment, the therapeutic agent in the coating layer overlying the surface of the balloon is rapamycin and analogues thereof.

In one embodiment, the concentration of the therapeutic agent in the coating layer is from 2.5 to 6 µg/mm$^2$.

In one embodiment, the additive in the coating layer overlying the surface of the balloon is an ionic or non-ionic surfactant. In another embodiment, the additive in the coating layer overlying the surface of the balloon is a vitamin or derivative thereof.

In one embodiment, the additive in the coating layer overlying the surface of the balloon is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly(glycidol), Octyl-betha-D-glycopyranoside, and deconoyl-N-methylglucamide. In another embodiment, the additive in the coating layer overlying the surface of the balloon is chosen from PEG fatty esters and alcohols, glycerol fatty esters, sorbitan fatty esters, PEG glyceryl fatty esters, PEG sorbitan fatty esters, sugar fatty esters, PEG sugar esters, vitamins and derivatives, amino acids, multi amino acids and derivatives, peptides, polypeptides, proteins, quaternary ammonium salts, organic acids, salts and anhydrides.

In another embodiment, the additive in the coating layer overlying the surface of the balloon is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), L-ascorbic acid and its salt, D-glucoascorbic acid and its salt, tromethamine, glucamine, glucoheptonic acid, glucomic acid, gluconolactone, glucosamine, glutamic acid, polyglycidol, glycerols and multiglycerols (chemical compounds with multiple hydroxyl, amino, carbonyl, carboxyl, or ester moieties). In yet another embodiment, the additive in the coating layer overlying the surface of the balloon is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the balloon catheter further comprises a dimethylsulfoxide solvent layer overlying the coating layer, wherein the dimethylsulfoxide layer enhances the ability of the therapeutic agent to penetrate into the blood vessel. In another embodiment, the balloon catheter further comprises an adherent layer between the exterior surface of the balloon and the coating layer. In yet another embodiment, the balloon catheter further comprises a top layer overlying the coating layer, wherein the top layer prevents loss of the therapeutic agent during transit through a body to the blood vessel.

In yet a further embodiment, the present invention relates to a pharmaceutical composition for treating a diseased body lumen or cavity after a surgical or interventional procedure, wherein the composition comprises a therapeutic agent and an additive, wherein the additive comprises a hydrophilic part and a hydrophobic part, wherein the therapeutic agent is not enclosed in micelles or encapsulated in polymer particles, and wherein the composition does not include an iodine covalent bonded contrast agent.

In yet a further embodiment, the present invention relates to a method for treating a diseased body lumen or cavity after a surgical or interventional procedure comprising delivering a pharmaceutical composition at a surgical site by injection or spraying with a catheter, wherein the composition comprises a therapeutic agent and an additive, wherein the additive comprises a hydrophilic part and a hydrophobic part, wherein the therapeutic agent is not enclosed in micelles or encapsulated in polymer particles, and wherein the composition does not include an iodine covalent bonded contrast agent.

In yet a further embodiment, the present invention relates to a pharmaceutical composition for treating a cancer including cancers of the ovary, breast, lung, esophagus, head and neck region, bladder, brain, liver, colon and lymphomas, wherein the composition comprises a therapeutic agent and an additive, wherein the additive comprises a hydrophilic part and a hydrophobic part, wherein the therapeutic agent is not enclosed in micelles or encapsulated in polymer particles, and wherein the composition does not include an iodine covalent bonded contrast agent. In one aspect of this embodiment, the therapeutic agent is chosen from paclitaxel and analogues thereof and rapamycin and analogues thereof.

In yet a further embodiment, the present invention relates to a solution for coating a medical device. In one aspect of this embodiment, the solution comprises an organic solvent, a therapeutic agent, and an additive, wherein the additive comprises a hydrophilic part and a hydrophobic part, wherein the therapeutic agent is not enclosed in micelles or encapsulated in polymer particles, and wherein the solution does not include an iodine covalent bonded contrast agent. In one aspect of this embodiment, the solution does not include a purely hydrophobic additive. In another aspect of this embodiment, the solution does not contain a dye. In another embodiment, the solution for coating a medical device does not include oil, a lipid, or a polymer.

In one embodiment, the additive in the coating solution is an ionic or non-ionic surfactant. In another embodiment, the additive is a vitamin or derivative thereof.

In one embodiment, the additive in the coating solution is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly(glycidol), Octyl-betha-D-glycopyranoside, and deconoyl-N-methylglucamide.

In another embodiment, the additive in the coating solution is chosen from PEG fatty esters and alcohols, glycerol fatty esters, sorbitan fatty esters, PEG glyceryl fatty esters, PEG sorbitan fatty esters, sugar fatty esters, PEG sugar esters, vitamins and derivatives, amino acids, multi amino acids and derivatives, peptides, polypeptides, proteins, quaternary ammonium salts, organic acids, salts and anhydrides.

In another embodiment, the additive in the coating solution is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases (proteins), benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), L-ascorbic acid and its salt, D-glucoascorbic acid and its salt, tromethamine, glucamine, glucoheptonic acid, glucomic acid, gluconolactone, glucosamine, glutamic acid (chemical compounds with multiple hydroxyl, amino, carbonyl, carboxyl, or ester moieties).

In another embodiment, the additive in the solution is chosen from sorbirtan troleate, and sorbitan fatty esters. In yet another embodiment, the additive in the coating solution is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the therapeutic agent in the coating solution is paclitaxel or rapamycin.

In one embodiment, the content of the therapeutic agent in the solution is from 0.5-50% by weight. In one embodiment, the content of the additive in the coating solution is from 1-45% by weight.

In one embodiment, the additive in the solution is soluble in aqueous solvent and is soluble in organic solvent.

In yet a further embodiment, the present invention relates to a medical device for delivering a therapeutic agent to a tissue, the device comprising a first layer applied to an exterior surface of the medical device, and a second layer overlying the first layer. In one aspect of this embodiment, the first layer comprises a therapeutic agent, and the second layer comprises an additive, wherein the additive comprises a hydrophilic part and a hydrophobic part, and wherein the therapeutic agent in the first layer is not enclosed in micelles or encapsulated in polymer particles. In one aspect of this embodiment, the first layer further comprises an additive. In another aspect of this embodiment, the second layer further comprises a therapeutic agent. In yet a further aspect of this embodiment, the first layer further comprises an additive and the second layer further comprises a therapeutic agent.

In a further embodiment, the present invention relates to a two layer coating comprising a first layer comprising a therapeutic agent, and a second layer comprising an additive. In one aspect of this embodiment, the second layer may be overlying the first layer. In one aspect of this embodiment, the additive in the second layer comprises a hydrophilic part and a hydrophobic part, and the therapeutic agent in the first layer is not enclosed in micelles or encapsulated in polymer particles. In one aspect of this embodiment, the first layer further comprises an additive. In another aspect of this embodiment, the second layer further comprises a therapeutic agent. In yet another aspect of this embodiment, the first layer further comprises an additive and the second layer further comprises a therapeutic agent.

In a further embodiment, the present invention relates to a method for preparing a medical device. In one aspect of this embodiment, the method comprises (a) preparing a coating solution comprising an organic solvent, a therapeutic agent, and an additive, wherein the additive comprises a hydrophilic part and a hydrophobic part, and wherein the therapeutic agent is not enclosed in micelles or encapsulated in polymer particles, and wherein the solution does not include an iodine covalent bonded contrast agent, (b) applying the coating solution to a medical device, and (c) drying the coating solution, forming a coating layer. In one aspect of this embodiment, the coating is applied by dipping a portion of the exterior surface of the medical device in the coating solution. In another aspect of this embodiment, the coating is applied by spraying a portion of the exterior surface of the medical device with a coating solution. In another aspect of this embodiment, steps (b) and (c) are repeated until a therapeutically effective amount of the therapeutic agent in the coating layer is deposited on the surface of the medical device. In another aspect of this embodiment, the total thickness of the coating layer is from about 0.1 to 200 microns. In another aspect of this embodiment, the concentration density of the at least one therapeutic agent applied to the surface of the medical device is from about 1 to 20 $\mu g/mm^2$, or in another aspect from about 2 to 6 $\mu g/mm^2$. In yet another aspect of this embodiment, the method further comprises applying a dimethylsulfoxide solvent to the dried coating layer obtained in (c).

In another embodiment, the method for preparing the medical device comprises, (a) preparing a coating solution comprising an organic solvent, a therapeutic agent, and an additive, wherein the additive is an anhydride, (b) applying the coating solution to a medical device, (c) drying the coating solution, forming a coating layer, and (d) hydrolyzing the anhydride to an acid group.

In a further embodiment, the present invention relates to a method for preparing a drug coated balloon catheter. In one aspect of this embodiment, the method comprises, (a) preparing a coating solution comprising an organic solvent, a therapeutic agent, and an additive, wherein the coating solution does not include an iodine covalent bonded contrast agent or a dye, (b) applying the coating solution to an inflated balloon catheter, and (c) deflating and folding the balloon catheter and drying the coating solution to increase uniformity of drug coating.

In a further embodiment, the present invention relates to a method for treating a blood vessel. In one aspect of this embodiment, the method comprises inserting a medical device comprising a coating layer into the blood vessel, wherein the coating layer comprises a therapeutic agent and an additive, wherein the additive comprises a hydrophilic part and a hydrophobic part, wherein the coating layer does not include an iodine covalent contrast agent or a dye, and wherein the therapeutic agent is not enclosed in micelles or encapsulated in polymer particles, and releasing the therapeutic agent into the tissue of the blood vessel in 2 minutes or less.

In a further embodiment, the present invention relates to a method for treating a total occlusion of body passages. In one aspect of this embodiment, the method comprises removing plaques in the body passages by one of a debulking catheter, a laser atherectomy, a directing atherectomy, or a rotational atherectomy, inserting a medical device comprising a coating layer into the body passages, wherein the coating layer comprises a therapeutic agent and an additive, wherein the additive comprises a hydrophilic part and a hydrophobic part, and wherein the coating layer does not include an iodine covalent contrast agent or a dye, and releasing the therapeutic agent into the tissue of the body passage or lumen, such as a blood vessel, in 2 minutes or less.

In a further embodiment, the present invention relates to a method for treating tissue of a body comprising bringing a medical device comprising a coating layer into contact with tissue of the body, wherein the coating layer comprises a therapeutic agent and an additive, wherein the additive comprises a hydrophilic part and a hydrophobic part, and wherein the coating layer does not include an iodine covalent contrast agent or a dye, and releasing the therapeutic agent into the tissue in 2 minutes or less. In one aspect of this embodiment, the tissue includes tissue of one of coronary vasculature, peripheral vasculature, cerebral vasculature, esophagus, airways, sinus, trachea, colon, biliary tract, urinary tract, prostate, and brain passages.

In yet a further embodiment, the present invention relates to a process of producing a balloon catheter. In one aspect of this embodiment, the process comprises preparing a solution comprising an organic solvent, a therapeutic agent, and an additive, wherein the additive comprises a hydrophilic part and a hydrophobic part, and wherein the therapeutic agent is not enclosed in micelles or encapsulated in polymer particles, applying the solution to the balloon catheter, and evaporating the solvent.

In yet a further embodiment, the present invention relates to a medical device comprising a layer overlying an exterior surface of the medical device, the layer comprising a therapeutic agent and an additive, wherein the additive is one of PEG fatty ester, PEG fatty ether, and PEG fatty alcohols. In one aspect of this embodiment, the additive is chosen from PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, PEG-20 oleate, PEG-20 dilaurate, PEG-20 dioleate, PEG-20 distearate, PEG-32 dilaurate and PEG-32 dioleate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is one of glycerol and polyglycerol fatty esters and PEG glycerol fatty esters. In one aspect of this embodiment, the additive is chosen from polyglyceryl oleate, polyglyceryl-2 dioleate, polyglyceryl-10 trioleate, polyglyceryl stearate, polyglyceryl laurate, polyglyceryl myristate, polyglyceryl palmitate, polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, polyglyceryl polyricinoleates, PEG-20 glyceryl laurate, PEG-30 glyceryl laurate, PEG-40 glyceryl laurate, PEG-20 glyceryl oleate, and PEG-30 glyceryl oleate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical comprising a layer overlying an exterior surface of the medical device, the layer comprising a therapeutic agent and an additive, wherein the additive is one of sorbitan fatty esters, and PEG sorbitan esters. In one aspect of this embodiment, the additive is chosen from sorbitan monolaurate, sorbitan monopalmitate, sorbitan monooleate, sorbitan monostearate, PEG-20 sorbitan monolaurate, PEG-20 sorbitan monopalmitate, PEG-20 sorbitan monooleate, and PEG-20 sorbitan monostearate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is a chemical compound containing a phenol moiety. In one aspect of this embodiment, the additive is chosen from p-isononylphenoxypolyglycidol, octoxynol, monoxynol, tyloxapol, octoxynol-9, and monoxynol-9. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is a sugar or sugar derivative. In one aspect of this embodiment, the additive is chosen from sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside, D-glucoascorbic acid and its salt, tromethamine, glucamine, glucoheptonic acid, glucomic acid, gluconolactone, and glucosamine. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is an ionic surfactant. In one aspect of this embodiment, the additive is chosen from benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is a vitamin or vitamin derivative. In one aspect of this embodiment, the additive is chosen from acetiamine, benfotiamine, pantothenic acid, cetotiamine, cyclothiamine, dexpanthenol, niacinamide, nicotinic acid and its salts, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, vitamin U, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is an amino acid, an amino acid salt, or an amino acid derivative. In one aspect of this embodiment, the additive is chosen from alanine, arginine, asparagine, aspartic acid, cysteine, glutamic acid, glutamine, glycine, histidine, proline, isoleucine, leucine, lysine, methionine, phenylalanine, serine, threonine, tryptophan, tyrosine, valine, and their derivatives. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device for delivering a therapeutic agent to a tissue, the device comprising a layer overlying an exterior surface of the medical device, the layer comprising a therapeutic agent and an additive, wherein the additive is a peptide, oligopeptide, or protein. In one aspect of this embodiment, the additive is chosen from albumins, immunoglobulins, caseins, hemoglobins, lysozymes, immunoglobins, a-2-macroglobulin, fibronectins, vitronectins, firbinogens, and lipases. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device for delivering a therapeutic agent to a tissue, the device comprising a layer overlying an exterior surface of the medical device, the layer comprising a therapeutic agent and an additive, wherein the additive is an organic acid or an organic acid ester or anhydride. In one aspect of this embodiment, the additive is chosen from acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic acid and anhydride, glutaric acid and anhydride, ascorbic acid, citric acid, tartaric acid, lactic acid, oxalic acid aspartic acid, nicotinic acid, and 2-pyrrolidone-5-carboxylic acid. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

It is understood that both the foregoing general description and the following detailed description are exemplary and explanatory only and are not restrictive of the present invention as claimed.

DETAILED DESCRIPTION OF EXEMPLARY EMBODIMENTS

Embodiments of the present invention relate to medical devices, including particularly balloon catheters and stents, having a rapid drug-releasing coating and methods for preparing such coated devices. The therapeutic agent according to embodiments of the present invention does not require a delayed or long term release and instead preferably is released in a very short time period to provide a therapeutic effect upon contact with tissue. An object of embodiments of the present invention is to facilitate rapid and efficient uptake of drug by target tissue during transitory device deployment at a target site.

Figure 1:
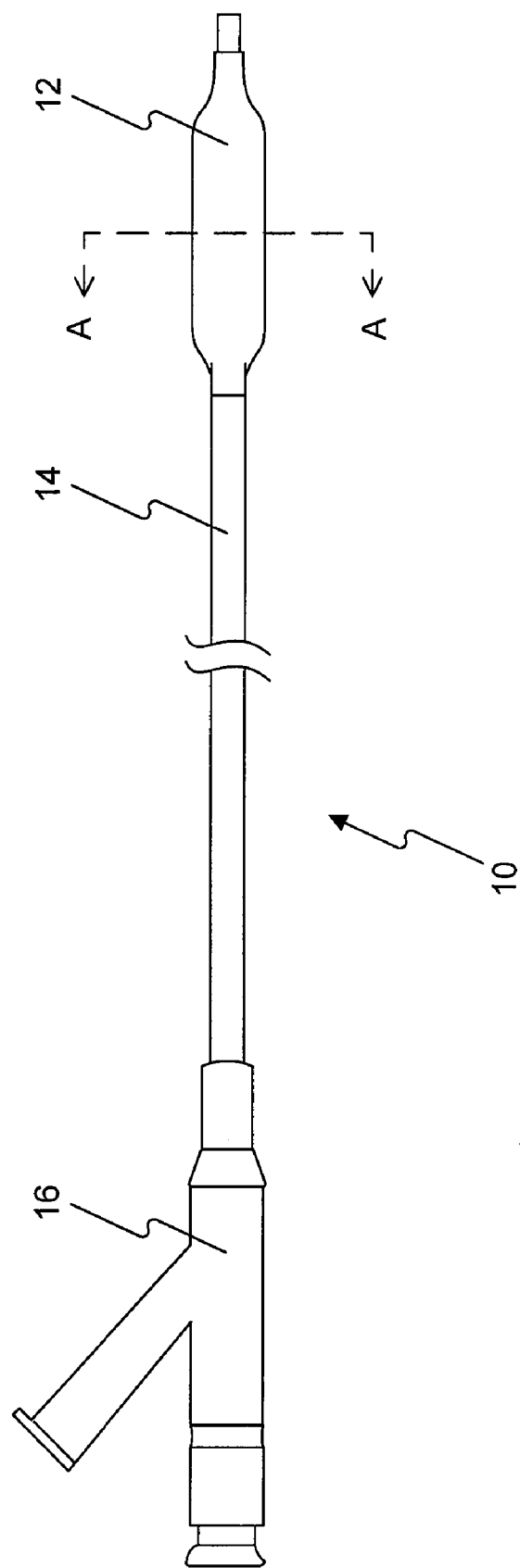
FIG. 1 is a perspective view of an exemplary embodiment of a balloon catheter according to the present invention.

As shown in FIG. 1, in one embodiment, the medical device is a balloon catheter. The balloon catheter may be any suitable catheter for the desired use, including conventional balloon catheters known to one of ordinary skill in the art. For example, balloon catheter 10 may include an expandable, inflatable balloon 12 at a distal end of the catheter 10, a handle assembly 16 at a proximal end of the catheter 10, and an elongate flexible member 14 extending between the proximal and distal ends. Handle assembly 16 may connect to and/or receive one or more suitable medical devices, such as a source of inflation media (e.g., air, saline, or contrast media). Flexible member 14 may be a tube made of suitable biocompatible material and having one or more lumens therein. At least one of the lumens is configured to receive inflation media and pass such media to balloon 12 for its expansion. The balloon catheter may be a rapid exchange or over-the-wire catheter and made of any suitable biocompatible material.

Figure 2A:
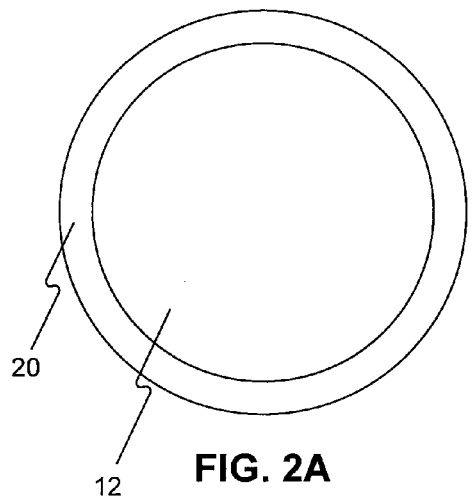
FIGS. 2A-2C are cross-sectional views of different embodiments of the distal portion of the balloon catheter of FIG. 1, taken along line A-A, showing exemplary coating layers.
Figure 2B:
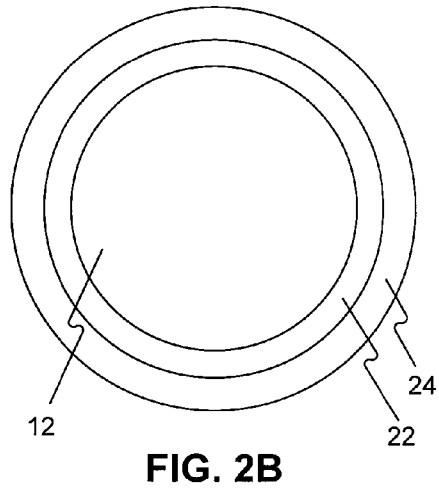

In one embodiment, the present invention provides a medical device for delivering a therapeutic agent to a tissue. The device includes a layer applied to an exterior surface of the medical device, such as a balloon catheter or stent, for example. The layer includes a therapeutic agent and an additive. For example, as shown in the embodiment depicted in FIG. 2A, the balloon 12 is coated with a layer 20 that includes a therapeutic agent and an additive. In some embodiments, the layer consists essentially of a therapeutic agent and an additive, i.e., the layer includes only the therapeutic agent and the additive, without any other materially significant components. In some embodiments, the device may optionally include an adherent layer. For example, as shown in the embodiment depicted in FIG. 2B, the balloon 12 is coated with an adherent layer 22. A layer 24 that includes a therapeutic agent and an additive is overlying the adherent layer. The adherent layer, which is a separate layer underlying the drug coating layer, improves the adherence of the drug coating layer to the exterior surface of the medical device and protects coating integrity. For example, if drug and additive differ in their adherence to the medical device, the adherent layer may prevent differential loss of components and maintain drug-to-additive ratio in the coating during transit to a target site for therapeutic intervention. Furthermore, the adherent layer may function to facilitate rapid release of coating layer components off the device surface upon contact with tissues at the target site.

In one embodiment, the concentration density of the at least one therapeutic agent applied to the surface of the medical device is from about 1 to 20 $\mu g/mm^2$, or more preferably from about 2 to 6 $\mu g/mm^2$. The ratio by weight of the additive to the therapeutic agent in the layer is from about 0.05 to 100, for example, from about 0.1 to 5, from 0.5 to 2, and further for example, from about 0.8 to 1.2

In other embodiments, the layer may include a therapeutic agent and more than one additive. For example, one additive may serve to improve balloon adhesion of another additive or additives that are superior at promoting tissue uptake of drug.

In other embodiments, the layer may include at least one therapeutic agent, at least one additive, and at least one polymer carrier for coating of a medical device such as a stent or a balloon. The therapeutic agent is not encapsulated in polymer particles. The additive in the layer improves compatibility of the drug and polymer carrier. It reduces the size or eliminates drug crystal particles in the polymer matrix of the coating. The uniform drug distribution in the coating improves clinical outcomes by more uniformly delivering drug to target tissues.

In another embodiment, the device comprises two layers applied to an exterior surface of the medical device, and particularly a balloon catheter, for example. The first layer comprises a therapeutic agent. The first layer may optionally comprise an additive or additives. The second layer comprises an additive or additives. The second layer may optionally include at least a therapeutic agent. When the first and second layers both contain a therapeutic agent, the content of the therapeutic agent in the second layer is lower than the content of the therapeutic agent in the first layer. In one embodiment, the second layer is overlying the first layer. In this arrangement, the second layer can prevent drug loss during deployment of the medical device into body passageways, for example, as a balloon catheter traverses the tortuous anatomy to a tissue site in the vasculature.

In another embodiment, the device comprises two layers applied to an exterior surface of the medical device, and particularly a balloon catheter, for example. The first layer comprises a therapeutic agent. The first layer may optionally comprise an additive or additives. The second layer comprises an additive or additives. The second layer may optionally include at least a therapeutic agent. When the first and second layers both contain a therapeutic agent, the content of the therapeutic agent in the first layer is lower than the content of the therapeutic agent in the second layer. In one embodiment, the second layer is overlying the first layer. This arrangement is useful, for example, in the case of a therapeutic agent that adheres too tightly to the balloon surface to rapidly elute off the balloon when inflated at the target site. In this arrangement, the first layer functions to facilitate rapid release of the bulk of drug, which is in the second layer, off the surface of the device while it is inflated at the target site of therapeutic intervention.

In other embodiments, two or more therapeutic agents are used in combination in the drug-additive layer.

Figure 2C:
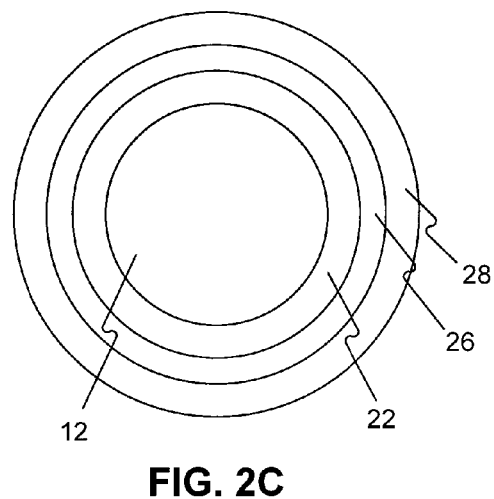

In a further embodiment, the device having a two layer coating may optionally include an adherent layer. The adherent layer does not contain a therapeutic agent. For example, as shown in the embodiment depicted in FIG. 2C, the balloon 12 is coated with an adherent layer 22. A first layer 26 that comprises a therapeutic agent and optionally an additive or additives is overlying the adherent layer 22. A second layer 28 that comprises an additive and optionally a therapeutic agent is overlying the first layer 26. The adherent layer improves the adherence of the first layer to the exterior surface of the medical device and protects the integrity of the first layer. For example, if drug and additive or additives in the first layer differ in their strength of adherence to the medical device, the adherent layer may prevent differential loss of components and maintain drug-to-additive and additive-to-additive ratio in the first and second layers during transit to a target site for therapeutic intervention. Furthermore, the adherent layer may function to facilitate rapid elution of coating layer off the device surface upon contact with tissues at the target site. In one embodiment, the first layer, the second layer, and the adherent layer each contain an additive.

Optionally, post-treatment with dimethylsulfoxide (DMSO) or other solvent may be advantageous since DMSO may further enhance penetration and absorption of drug into tissue. DMSO displaces water from the lipid head groups and protein domains of the membrane lipid bilayer of target cells to indirectly loosen the lipid structure, accelerating drug absorption and penetration.

In a further embodiment, the present invention relates to a pharmaceutical composition for treating a diseased body lumen or cavities after surgical or interventional procedures (PTCA, PTA, stent placement, excision of diseased tissue such as cancer, and relieving or treating stenosis), wherein the pharmaceutical composition comprises a therapeutic agent and an additive, wherein the additive comprises a hydrophilic part and a hydrophobic part, and wherein the therapeutic agent is not enclosed in micelles or encapsulated in polymer particles.

In another embodiment, a method of preventing complications or recurrence of disease (such as cancer or restenosis) after a surgical or interventional procedure such as PTCA, PTA, stent deployment, stenosis or plaque removal by debulking, atherectomy, or laser procedures, the pharmaceutical composition is locally delivered at or near the site of intervention by means of a coated medical device (such as a drug-coated balloon), or by spray, by injection, or by deposition. For example, the pharmaceutical composition may be delivered by spray, injection, balloon or other method of deposition, into cavities created by surgical removal of cancer tissue in order to reduce the risk of recurrence. As another example, a method for delivering the pharmaceutical composition comprises inserting a medical device (such as guide catheter or a drug infusion catheter) into the blood to inject the pharmaceutical composition after a vascular intervention such as PTCA, PTA, or stent placement to prevent restenosis, wherein the pharmaceutical composition comprises a therapeutic agent and an additive, wherein the additive comprises a hydrophilic part and a hydrophobic part, and wherein the therapeutic agent is not enclosed in micelles or encapsulated in polymer particles.

Additive

The additive of the present invention has two parts. One part is hydrophilic and the other part is hydrophobic or lipophilic. The hydrophobic or lipophilic part of the additive may bind the lipophilic drug, such as rapamycin or paclitaxel. The hydrophilic portion accelerates diffusion and increases permeation of the drug into tissue. It may facilitate rapid movement of drug off the medical device during deployment and into interstitial space and through polar head groups to the lipid bilayer of cell membranes of target tissues.

In embodiments of the present invention, the therapeutic agent is rapidly released after the medical device is brought into contact with tissue and is readily absorbed.

The additive has a lipophilic or hydrophobic part and a hydrophilic part. The hydrophobic part may include aliphatic and aromatic organic hydrocarbon compounds, such as benzene, toluene, and alkanes, among others. These parts are not water soluble. They may bind both hydrophobic drug, with which they share structural similarities, and lipids of cell membranes. They have no covalently bonded iodine. The hydrophilic part may include hydroxyl groups, amine groups, amide groups, carbonyl groups, carboxylic acid and anhydrides, ethyl oxide, ethyl glycol, polyethylene glycol, ascorbic acid amino acid, amino alcohol, glucose, sucrose, sorbitan, glycerol, polyalcohol, phosphates, sulfates, organic salts and their substituted molecules, among others. Multiple hydroxyl, carboxyl, or amine groups, for example, may be advantageous since they easily displace water molecules that are hydrogen-bound to polar head groups and surface proteins of cell membranes and may function to remove this barrier between hydrophobic drug and cell membrane lipid. These parts can dissolve in water and polar solvents. These additives are not oils, lipids, or polymers. The therapeutic agent is not enclosed in micelles or liposomes or encapsulated in polymer particles. The additive of embodiments of the present invention have hydrophobic and hydrophilic components to both bind drug and facilitate its rapid movement off the medical device during deployment and into target tissues.

As is well known in the art, the terms "hydrophilic" and "hydrophobic" are relative terms. To function as an additive in exemplary embodiments of the present invention, the compound includes polar or charged hydrophilic moieties as well as non-polar hydrophobic (lipophilic) moieties.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute]octanol/[solute]water). Compounds with higher log Ps are more hydrophobic, while compounds with lower log Ps are more hydrophilic. Lipinski's rule suggests that pharmaceutical compounds having log P<5 are typically more membrane permeable. While a compound's octanol-water partition coefficient P or log P is useful as a measurement of relative hydrophilicity and hydrophobicity, it is merely a rough guide that may be useful in defining suitable additives for use in embodiments of the present invention.

Suitable additives that can be used in embodiments of the present invention include, without limitation, organic and inorganic pharmaceutical excipients, natural products and their derivatives (such as sugars, vitamins, amino acids, peptides, proteins, fatty acids), low molecular weight oligomers, surfactants (anionic, cationic, non-ionic, and ionic), and mixtures thereof. The following detailed list of additives useful in the present invention is provided for exemplary purposes only and is not intended to be comprehensive. Many other additives may be useful for purposes of the present invention.

Surfactants

The surfactant can be any surfactant suitable for use in pharmaceutical compositions. Such surfactants can be anionic, cationic, zwitterionic or non-ionic. Mixtures of surfactants are also within the scope of the invention, as are combinations of surfactant and other additives. Surfactants often have one or more long aliphatic chains such as fatty acids that may insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10.

It should be understood that the HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants may be identified that have suitable hydrophilicity or hydrophobicity for use in embodiments of the present invention, as described herein.

PEG-Fatty Acids and PEG-Fatty Acid Mono and Diesters

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Most preferred hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and diesters.

Polyethylene Glycol Glycerol Fatty Acid Esters

Preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products

A large number of surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® b M 2735 CS), PEG-8 corn oil (Labrafil® WL 2609 BS), PEG-20 corn glycerides (Crovol M40), and PEG-20 almond glycerides (Crovol A40).

Polyglyceryl Fatty Acids

Polyglycerol esters of fatty acids are also suitable surfactants for use in embodiments of the present invention. Among the polyglyceryl fatty acid esters, preferred hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also preferred surfactants.

Propylene Glycol Fatty Acid Esters

Esters of propylene glycol and fatty acids are suitable surfactants for use in embodiments of the present invention. In this surfactant class, preferred hydrophobic surfactants include propylene glycol monolaurate (Lauroglycol FCC), propylene glycol ricinoleate (Propymuls), propylene glycol monooleate (Myverol P-O6), propylene glycol dicaprylate/dicaprate (Captex® 200), and propylene glycol dioctanoate (Captex® 800).

Sterol and Sterol Derivatives

Sterols and derivatives of sterols are suitable surfactants for use in embodiments of the present invention. Preferred derivatives include the polyethylene glycol derivatives. A preferred surfactant in this class is PEG-24 cholesterol ether (Solulan C-24).

Polyethylene Glycol Sorbitan Fatty Acid Esters

A variety of PEG-sorbitan fatty acid esters are available and are suitable for use as surfactants in embodiments of the present invention. Among the PEG-sorbitan fatty acid esters, preferred surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80).

Polyethylene Glycol Alkyl Ethers

Ethers of polyethylene glycol and alkyl alcohols are suitable surfactants for use in embodiments of the present invention. Preferred ethers include PEG-3 oleyl ether (Volpo 3) and PEG-4 lauryl ether (Brij 30).

Sugar and its Derivatives

Sugar derivatives are suitable surfactants for use in embodiments of the present invention. Preferred surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, and octyl-β-D-thioglucopyranoside.

Polyethylene Glycol Alkyl Phenols

Several PEG-alkyl phenol surfactants are available, such as PEG-10-100 nonyl phenol and PEG-15-100 octyl phenol ether, Tyloxapol, octoxynol, nonoxynol, and are suitable for use in embodiments of the present invention.

Polyoxyethylene-Polyoxypropylene (POE-POP) Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)_b(C_2H_4O)_aH$ where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Sorbitan Fatty Acid Esters

Sorbitan esters of fatty acids are suitable surfactants for use in embodiments of the present invention. Among these esters, preferred hydrophobic surfactants include sorbitan monolaurate (Arlacel 20), sorbitan monopalmitate (Span-40), sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). And second, when the pH increases so as to convert a fraction of the ascorbyl palmitate to a more soluble salt, such as sodium ascorbyl palmitate.

Ionic Surfactants

Ionic surfactants, including cationic, anionic and zwitterionic surfactants, are suitable hydrophilic surfactants for use in embodiments of the present invention. Preferred ionic surfactants include quaternary ammonium salts, fatty acid salts and bile salts. Specifically, preferred ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate. These quaternary ammonium salts are preferred additives. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents.

Fat-Soluble Vitamins and Salts Thereof

Vitamins A, D, E and K in many of their various forms and provitamin forms are considered as fat-soluble vitamins and in addition to these a number of other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention.

The following examples of fat-soluble vitamin derivatives and/or sources are also useful as additives: Alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). Folic acid is also of this type, and although it is water-soluble at physiological pH, it can be formulated in the free acid form. Other derivatives of fat-soluble vitamins useful in embodiments of the present invention may easily be obtained via well known chemical reactions with hydrophilic molecules.

Water-Soluable Vitamins and Their Amphiphilic Derivatives

Vitamins B, C, U, pantothenic acid, folic acid, and some of the menadione-related vitamins/provitamins in many of their various forms are considered water-soluble vitamins. These may also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and Their Salts

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and their derivatives are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has a solubility in unbuffered water of less than about 4% (40 mg/ml). These include Cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well known in the art hydrophilic molecules may be joined to hydrophobic amino acids, or hydrophobic molecules to hydrophilic amino acids, to make additional additives useful in embodiments of the present invention.

Catecholamines, such as dopamine, levodopa, carbidopa, and DOPA, are also useful as additives.

Oligopeptides, Peptides and Proteins

Oligopeptides and peptides are useful as additives, since hydrophobic and hydrophilic amino acids may be easily coupled and various sequences of amino acids may be tested to maximally facilitate permeation of tissue by drug.

Proteins are also useful as additives in embodiments of the present invention. Serum albumin, for example, is a particularly preferred additive since it is water soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human intravascular use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and Their Esters and Anhydrides

Examples are acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methylethylketone, ethylacetate. The water insoluble drugs can be dissolved in organic solvent with these esters and anhydrides, then coated easily on to the medical device, then hydrolyzed under high pH conditions. The hydrolyzed anhydrides or esters are acids or alcohols, which are water soluble and can effectively carry the drugs off the device into the vessel walls.

Chemical Compounds with Multiple Hydroxyl, Amine, Carbonyl, Carboxyl, or Ester Moieties Examples are L-ascorbic acid and its salt, D-glucoascorbic acid and its salt, tromethamine, glucamine, glucoheptonic acid, glucomic acid, gluconolactone, glucosamine, glutamic acid, polyglycidol, glycerols and multiglycerols.

Preferred additives include p-isononylphenoxypolyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); cetotiamine; cyclothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, glucamine, glucoheptonic acid, glucomic acid, gluconolactone, glucosamine, glutamic acid, polyglycidol, glycerols and multiglycerols (chemical compounds with multiple hydroxyl, amino, carbonyl, carboxyl, or ester moieties). Some of these additives are both water-soluble and organic solvent-soluble. They have good adhesive properties and adhere to the surface of polyamide medical devices, such as balloon catheters. They may therefore be used in both the adherent layer and in the drug layer of embodiments of the present invention. The aromatic and aliphatic groups increase the solubility of water insoluble drugs in the coating solution, and the polar groups of alcohols and acids accelerate drug permeation of tissue.

Other preferred additives that may be useful in embodiments of the present invention include riboflavin, riboflavin-phosphate sodium, Vitamin D3, folic acid (vitamin B9), vitamin 12, diethylenetriaminepentaacetic acid dianhydride, ethylenediaminetetraacetic dianhydride, maleic acid and anhydride, succinic acid and anhydride, diglycolic anhydride, glutaric anhydride, L-ascorbic acid, thiamine, nicotinamide, nicotinic acid, 2-pyrrolidone-5-carboxylic acid, cystine, tyrosine, tryptophan, leucine, isoleucine, phenylalanine, asparagine, aspartic acid, glutamic acid, and methionine.

From a structural point of view, these additives share structural similarities and are compatible with water insoluble drugs (such as paclitaxel and rapamycin). They often contain double bonds such as C=C, C=N, C=O in aromatic or aliphatic structures. These additives also contain amine, alcohol, ester, amide, anhydride, carboxylic acid, and/or hydroxyl groups. Compounds containing multiple hydroxyl, carboxyl, or amine groups, for example, are especially useful as additives since they easily displace water next to the polar head groups and surface proteins of cell membranes and may remove this barrier to hydrophobic drug permeability. They thereby accelerate movement of a hydrophobic drug to the lipid layer of cell membranes, to which it has very high affinity. They may also carry or accelerate the movement of drug off the balloon into more aqueous environments such as the interstitial space, for example, of vascular tissues that have been injured by balloon angioplasty or stent expansion. Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic C=N groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for the vessel wall and can displace hydrogen-bound water molecules. At the same time, they have long chains of fatty acid, alcohol, ether and ester that can both complex with hydrophobic drug and integrate into the lipid structure of the cell membranes to form the part of the lipid structure. This deformation or loosening of the lipid membrane of target cells may further accelerate permeation of hydrophobic drug into tissue.

For another example, L-ascorbic acid, thiamine, maleic acids, niacinamide, and 2-pyrrolidone-5-carboxylic acid all have a very high water and ethanol solubility and a low molecular weight and small size. They may therefore penetrate tissue easily. They also have structural components including aromatic C=N, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore preferably used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

In embodiments of the present invention, the additive is soluble in aqueous solvents and is soluble in organic solvents. Extremely hydrophobic compounds that lack sufficient hydrophilic parts and are insoluble in aqueous solvent, such as the dye Sudan Red, are not useful as additives in these embodiments. Sudan red is also genotoxic.

In one embodiment, the concentration density of the at least one therapeutic agent applied to the surface of the medical device is from about 1 to 20 $\mu g/mm^2$, or more preferably from about 2 to 6 $\mu g/mm^2$. In one embodiment, the concentration of the at least one additive applied to the surface of the medical device is from about 1 to 20 $\mu g/mm^2$. The ratio of additives to drug by weight in the coating layer in embodiments of the present invention is about 20 to 0.05, preferably about 10 to 0.5, or more preferably about 5 to 0.8.

The relative amount of the therapeutic agent and the additive in the coating layer may vary depending on applicable circumstances. The optimal amount of the additive can depend upon, for example, the particular therapeutic agent and additive selected, the critical micelle concentration of the surface modifier if it forms micelles, the hydrophilic-lipophilic-balance (HLB) of a surfactant or an additive's the octonol-water partition coefficient (P), the melting point of the additive, the water solubility of the additive and/or therapeutic agent, the surface tension of water solutions of the surface modifier, etc.

The additives are present in exemplary coating compositions of embodiments of the present invention in amounts such that upon dilution with an aqueous solution, the carrier forms a clear, aqueous dispersion or emulsion or solution, containing the hydrophobic therapeutic agent in aqueous and organic solutions. When the relative amount of surfactant is too great, the resulting dispersion is visibly "cloudy".

The optical clarity of the aqueous dispersion can be measured using standard quantitative techniques for turbidity assessment. One convenient procedure to measure turbidity is to measure the amount of light of a given wavelength transmitted by the solution, using, for example, an UV-visible spectrophotometer. Using this measure, optical clarity corresponds to high transmittance, since cloudier solutions will scatter more of the incident radiation, resulting in lower transmittance measurements.

Another method of determining optical clarity and carrier diffusivity through the aqueous boundary layer is to quantitatively measure the size of the particles of which the dispersion is composed. These measurements can be performed on commercially available particle size analyzers.

Other considerations will further inform the choice of specific proportions of different additives. These considerations include the degree of bioacceptability of the additives and the desired dosage of hydrophobic therapeutic agent to be provided.

Therapeutic Agent

The drugs or biologically active materials, which can be used in embodiments of the present invention, can be any therapeutic agent or substance. The drugs can be of various physical states, e.g., molecular distribution, crystal forms or cluster forms. Examples of drugs that are especially useful in embodiments of the present invention are lipophilic substantially water insoluble drugs, such as paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature.

Other drugs that may be useful in embodiments of the present invention include, without limitation, glucocorticoids (e.g., dexamethasone, betamethasone), hirudin, angiopeptin, aspirin, growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents.

Also useful in embodiments of the present invention are polynucleotides, antisense, RNAi, or siRNA, for example, that inhibit inflammation and/or smooth muscle cell or fibroblast proliferation.

Anti-platelet agents can include drugs such as aspirin and dipyridamole. Aspirin is classified as an analgesic, anti-pyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present invention can include drugs such as heparin, protamine, hirudin and tick anticoagulant protein. Anti-oxidant agents can include probucol. Anti-proliferative agents can include drugs such as amlodipine and doxazosin. Anti-mitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, .beta.-sitosterin, ademetionine, myrtecaine, polidocanol, nonivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon a, .beta and y, histamine antagonists, serotonin blockers, apoptosis inhibitors, apoptosis regulators such as p65 NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamid, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyryl-mallotochromanol, maquiroside A, marchantin A, maytansine, lycoridicin, margetine, pancratistatin, liriodenine, bisparthenolidine, oxoushinsunine, aristolactam-All, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations may reduce complications from using a high dose of the drug.

Adherent Layer

The adherent layer, which is an optional layer underlying the drug coating layer, improves the adherence of the drug coating layer to the exterior surface of the medical device and protects coating integrity. If drug and additive differ in their adherence to the medical device, the adherent layer may prevent differential loss (during transit) or elution (at the target site) of drug layer components in order to maintain consistent drug-to-additive or drug-to-drug ratio in the drug layer and therapeutic delivery at the target site of intervention. Furthermore, the adherent layer may function to facilitate release of coating layer components which otherwise might adhere too strongly to the device for elution during brief contact with tissues at the target site. For example, in the case where a particular drug binds the medical device tightly, more hydrophilic components are incorporated into the adherent layer in order to decrease affinity of the drug to the device surface.

As described above, the adherent layer comprises a polymer or an additive or mixtures of both. The polymers that are useful for forming the adherent layer are ones that are biocompatible and avoid irritation of body tissue. Some examples of polymers that are useful for forming the adherent layer are polymers that are biostable, such as polyurethanes, silicones, and polyesters. Other polymers that are useful for forming the adherent layer include polymers that can be dissolved and polymerized on the medical device.

Some examples of polymers that are useful in the adherent layer of embodiments of the present invention include polyolefins, polyisobutylene, ethylene-α-olefin copolymers, acrylic polymers and copolymers, polyvinyl chloride, polyvinyl methyl ether, polyvinylidene fluoride and polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, and mixtures and block copolymers thereof.

Since the medical device undergoes mechanical manipulation, i.e., expansion and contraction, examples of polymers that are useful in the adherent layer include elastomeric polymers, such as silicones (e.g., polysiloxanes and substituted polysiloxanes), polyurethanes, thermoplastic elastomers, ethylene vinyl acetate copolymers, polyolefin elastomers, and EPDM rubbers. Due to the elastic nature of these polymers, when these polymers are used, the coating better adheres to the surface of the medical device when the device is subjected to forces or stress.

The adherent layer may also comprise one or more of the additives previously described, or other components, in order to maintain the integrity and adherence of the coating layer to the device and to facilitate both adherence of drug and additive components during transit and rapid elution during deployment at the site of therapeutic intervention.

Top Layer

In order to further protect the integrity of the drug layer, an optional top layer may be applied to prevent loss of drug during transit through tortuous anatomy to the target site.

Solvents

Solvents for the preparing of the coating layer may include, as examples, any combination of one or more of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/tetrahydrofuran.

Organic solvents, such as short-chained alcohol, dioxane, tetrahydrofuran, dimethylformamide, acetonitrile, dimethylsulfoxide, etc., are particularly useful and preferred solvents in embodiments of the present invention because these organic solvents generally disrupt collodial aggregates and co-solubilize all the components in the coating solution.

The therapeutic agent and additive or additives may be dispersed in, solubilized, or otherwise mixed in the solvent. The weight percent of drug and additives in the solvent may be in the range of 0.1-80% by weight, preferably 2-20% by weight.

Another embodiment of the invention relates to a method for preparing a medical device, particularly, for example, a balloon catheter or a stent. First, a coating solution or suspension comprising at least one solvent, at least one therapeutic agent, and at least one additive is prepared. In at least one embodiment, the coating solution or suspension includes only these three components. The content of the therapeutic agent in the coating solution can be from 0.5-50% by weight based on the total weight of the solution. The content of the additive in the coating solution can be from 1-45% by weight, 1 to 40% by weight, or from 1-15% by weight based on the total weight of the solution. The amount of solvent used depends on the coating process and viscosity. It will affect the uniformity of the drug-additive coating but will be evaporated.

In other embodiments, two or more solvents, two or more therapeutic agents, and/or two or more additives may be used in the coating solution.

In other embodiments, a therapeutic agent, an additive and a polymeric material may be used in the coating solution, for example in a stent coating. In the coating, the therapeutic agent is not encapsulated in polymer particles.

Various techniques may be used for applying a coating solution to a medical device such as casting, spinning, spraying, dipping (immersing), ink jet printing, electrostatic techniques, and combinations of these processes. Choosing an application technique principally depends on the viscosity and surface tension of the solution. In embodiments of the present invention, dipping and spraying are preferred because it makes it easier to control the uniformity of the thickness of the coating layer as well as the concentration of the therapeutic agent applied to the medical device. Regardless of whether the coating is applied by spraying or by dipping or by another method or combination of methods, each layer is usually deposited on the medical device in multiple application steps in order to control the uniformity and the amount of therapeutic substance and additive applied to the medical device.

Each applied layer is from about 0.1 microns to 15 microns in thickness. The total number of layers applied to the medical device is in a range of from about 2 to 50. The total thickness of the coating is from about 2 to 200 microns.

As discussed above, spraying and dipping are particularly useful coating techniques for use in embodiments of the present invention. In a spraying technique, a coating solution or suspension of an embodiment of the present invention is prepared and then transferred to an application device for applying the coating solution or suspension to a balloon catheter.

An application device that may be used is a paint jar attached to an air brush, such as a Badger Model 150, supplied with a source of pressurized air through a regulator (Norgren, 0-160 psi). When using such an application device, once the brush hose is attached to the source of compressed air downstream of the regulator, the air is applied. The pressure is adjusted to approximately 15-25 psi and the nozzle condition checked by depressing the trigger.

Prior to spraying, both ends of the relaxed balloon are fastened to the fixture by two resilient retainers, i.e., alligator clips, and the distance between the clips is adjusted so that the balloon remained in a deflated, folded, or an inflated or partially inflated, unfolded condition. The rotor is then energized and the spin speed adjusted to the desired coating speed, about 40 rpm.

With the balloon rotating in a substantially horizontal plane, the spray nozzle is adjusted so that the distance from the nozzle to the balloon is about 1-4 inches. First, the coating solution is sprayed substantially horizontally with the brush being directed along the balloon from the distal end of the balloon to the proximal end and then from the proximal end to the distal end in a sweeping motion at a speed such that one spray cycle occurred in about three balloon rotations. The balloon is repeatedly sprayed with the coating solution, followed by drying, until an effective amount of the drug is deposited on the balloon.

In one embodiment of the present invention, the balloon is inflated or partially inflated, the coating solution is applied to the inflated balloon, for example by spraying, and then the balloon is deflated and folded before drying. Drying may be performed under vacuum.

It should be understood that this description of an application device, fixture, and spraying technique is exemplary only. Any other suitable spraying or other technique may be used for coating the medical device, particularly for coating the balloon of a balloon catheter or stent delivery system or stent.

After the medical device is sprayed with the coating solution, the coated balloon is subjected to a drying in which the solvent in the coating solution is evaporated. This produces a coating matrix on the balloon containing the therapeutic agent. One example of a drying technique is placing a coated balloon into an oven at approximately 20° C. or higher for approximately 24 hours. Any other suitable method of drying the coating solution may be used. The time and temperature may vary with particular additives and therapeutic agents.

Optional Post Treatment

After depositing the drug-additive containing layer on the device of certain embodiments of the present invention, Dimethyl sulfoxide (DMSO) or other solvent may be applied, by dip or spray or other method, to the finished surface of the coating. DMSO readily dissolves drugs and easily penetrates membranes and may enhance tissue absorption.

It is contemplated that the medical devices of embodiments of the present invention have applicability for treating blockages and occlusions of any body passageways, including, among others, the vasculature, including coronary, peripheral, and cerebral vasculature, the gastrointestinal tract, including the esophagus, stomach, small intestine, and colon, the pulmonary airways, including the trachea, bronchi, bronchioles, the sinus, the biliary tract, the urinary tract, prostate and brain passages. They are especially suited for treating tissue of the vasculature with, for example, a balloon catheter or a stent.

Yet another embodiment of the present invention relates to a method of treating a blood vessel. The method includes inserting a medical device comprising a coating into a blood vessel. The coating layer comprises a therapeutic agent and an additive. In this embodiment, the medical device can be configured as having at least an expandable portion. Some examples of such devices include balloon catheters, perfusion balloon catheters, cutting balloon catheters, scoring balloon catheters, self-expanded and balloon expanded-stents, guide catheters, guide wires, embolic protection devices, and various imaging devices.

As mentioned above, one example of a medical device that is particularly useful in the present invention is a coated balloon catheter. A balloon catheter typically has a long, narrow, hollow tube tabbed with a miniature, deflated balloon. In embodiments of the present invention, the balloon is coated with a drug solution. Then, the balloon is maneuvered through the cardiovascular system to the site of a blockage, occlusion, or other tissue requiring a therapeutic agent. Once in the proper position, the balloon is inflated and contacts the walls of the blood vessel and/or a blockage or occlusion. It is an object of embodiments of the present invention to rapidly deliver drug to and facilitate absorption by target tissue. It is advantageous to efficiently deliver drug to tissue in as brief a period of time as possible while the device is deployed at the target site. The therapeutic agent is released into such tissue, for example the vessel walls, in about 0.1 to 30 minutes, for example, or preferably about 0.1 to 10 minutes, or more preferably about 0.2 to 2 minutes, or most preferably, about 0.1 to 1 minutes, of balloon inflation time pressing the drug coating into contact with diseased vascular tissue.

Given that a therapeutically effective amount of the drug can be delivered by embodiments of the present invention into, for example, the arterial wall, in some cases the need for a stent may be eliminated, obviating the complications of fracture and thrombosis associated therewith.

Should placement of a stent still be desired, a particularly preferred use for embodiments of the present invention is to crimp a stent, such as a bare metal stent (BMS), for example, over the drug coated balloon described in embodiments herein. When the balloon is inflated to deploy the stent at the site of diseased vasculature, an effective amount of drug is delivered into the arterial wall to prevent or decrease the severity of restenosis or other complications. Alternatively, the stent and balloon may be coated together, or the stent may be coated and then crimped on a balloon.

Further, the balloon catheter may be used to treat vascular tissue/disease alone or in combination with other methods for treating the vasculature, for example, photodynamic therapy or atherectomy. Atherectomy is a procedure to remove plaque from arteries. Specifically, atherectomy removes plaque from peripheral and coronary arteries. The medical device used for peripheral or coronary atherectomy may be a laser catheter or a rotablator or a direct atherectomy device on the end of a catheter. The catheter is inserted into the body and advanced through an artery to the area of narrowing. After the atherectomy has removed some of the plaque, balloon angioplasty using the coated balloon of embodiments of the present invention may be performed. In addition, stenting may be performed thereafter, or simultaneously with expansion of the coated balloon as described above. Photodynamic therapy is a procedure where light or irradiated energy is used to kill target cells in a patient. A light-activated photosensitizing drug may be delivered to specific areas of tissue by embodiments of the present invention. A targeted light or radiation source selectively activates the drug to produce a cytotoxic response and mediate a therapeutic anti-proliferative effect.

In some of the embodiments of drug-containing coatings and layers according to the present invention, however, the coating or layer does not include polymers, oils, or lipids. And, furthermore, the therapeutic agent is not encapsulated in polymer particles, micelles, or liposomes. As described above, such formulations have significant disadvantages and can inhibit the intended efficient, rapid release and tissue penetration of the agent, especially in the environment of diseased tissue of the vasculature.

Although various embodiments are specifically illustrated and described herein, it will be appreciated that modifications and variations of the present invention are covered by the above teachings and are within the purview of the appended claims without departing from the spirit and intended scope of the invention.

Other than the operating examples, or where otherwise indicated, all numbers expressing quantities of components in a layer, reaction conditions, and so forth used in the specification and claims are to be understood as being modified in all instances by the term "about." Accordingly, unless otherwise indicated to the contrary, the numerical parameters set forth in this specification and attached claims are approximations that may vary depending upon the desired properties sought to be obtained by the present disclosure.

Preparation

The medical device and the coating layers of embodiments of the present invention can be made according to various methods. For example, the coating solution can be prepared by dispersing, dissolving, diffusing, or otherwise mixing all the ingredients, such as a therapeutic agent, an additive, and a solvent, simultaneously together. Also, the coating solution can be prepared by sequentially adding each component based on solubility or any other parameters. For example, the coating solution can be prepared by first adding the therapeutic agent to the solvent and then adding the additive. Alternatively, the additive can be added to the solvent first and then the therapeutic agent can be later added. If the solvent used does not sufficiently dissolve the drug, it is preferable to first add the additive to the solvent, then the drug, since the additive will increase drug solubility in the solvent.

EXAMPLES

The following examples include embodiments of medical devices and coating layers within the scope of the present invention. While the following examples are considered to embody the present invention, the examples should not be interpreted as limitations upon the present invention.

Example 1

Preparation of Coating Solutions

Solution 1-50-150 mg (0.06-0.18 mmole) paclitaxel, 2-6 ml acetone (or ethanol), 25-100 mg ascorbyl palmitate, 25-100 mg L-ascorbic acid and 0.5 ml ethanol are mixed.

Solution 2-50-150 mg (0.05-0.16 mmole) rapamycin, 2-6 ml acetone (or ethanol), 50-200 mg polyglyceryl-10 oleate and 0.5 ml ethanol are mixed.

Solution 3-50-150 mg (0.06-0.18 mmole) paclitaxel, 2-6 ml acetone (or ethanol), 50-200 mg octoxynol-9 and 0.5 ml ethanol are mixed.

Solution 4-50-150 mg (0.05-0.16 mmole) rapamycin, 2-6 ml acetone (or ethanol), 50-200 mg p-isononylphenoxypolyglycidol and 0.5 ml ethanol are mixed.

Solution 5-50-150 mg (0.06-0.18 mmole) paclitaxel, 2-6 ml acetone (or ethanol), 50-200 mg Tyloxapol and 0.5 ml ethanol are mixed.

Solution 6-50-150 mg (0.05-0.16 mmole) rapamycin in 2-6 ml acetone (or ethanol), 50-150 mg L-ascorbic acid in 1 ml water or ethanol, both, then are mixed.

Solution 7-50-150 mg (0.06-0.18 mmole) paclitaxel, 2-6 ml acetone (or ethanol), 50-150 mg niacinamide in 1 ml water or ethanol, and both are mixed.

Solution 8-50-150 mg (0.05-0.16 mmole) rapamycin, 2-6 ml acetone (or ethanol), 50-200 mg nicotinic acid in 1 ml water or ethanol and both are mixed.

Solution 9-50-150 mg (0.06-0.18 mmole) paclitaxel, 2-6 ml ethanol (or acetone), 150 mg thiamine hydrochloride in 1 ml water, and 0.5 ml both are mixed.

Solution 10-50-150 mg (0.05-0.16 mmole) rapamycin, 2-6 ml acetone or ethanol, 150 mg 2-pyrrolidone-5-carboxylic acid in 1 ml water or ethanol, and both are mixed.

Solution 11-50-150 mg (0.06-0.18 mmole) paclitaxel, 2-6 ml acetone (or ethanol), 75 mg p-isononylphenoxypolyglycidol, 75 mg niacinamide in 1 ml water or ethanol, and 0.5 ml ethanol are mixed.

Solution 12-50-150 mg (0.05-0.16 mmole) rapamycin, 2-6 ml acetone (or ethanol), 75 mg Octoxynol-9, 75 mg thiamine hydrochloride in 1 ml water or ethanol, and 0.5 ml ethanol are mixed.

Solution 13-50-150 mg (0.06-0.18 mmole) paclitaxel, 2-6 ml acetone (or ethanol), 75 mg p-isononylphenoxypolyglycidol, 75 mg 2-pyrrolidone-5-carboxylic acid in 1 ml water or ethanol, and 0.5 ml ethanol are mixed.

Solution 14-50-150 mg (0.06-0.18 mmole) paclitaxel, 2-6 ml acetone (or ethanol), 75 mg p-isononylphenoxypolyglycidol, 75 mg nicotinic acid in 1 ml water or ethanol, and 0.5 ml ethanol are mixed.

Solution 15-50-150 mg (0.06-0.18 mmole) paclitaxel, 2-6 ml acetone (or ethanol), 75 mg p-isononylphenoxypolyglycidol, 75 mg L-ascorbic acid in 1 ml water or ethanol, and 0.5 ml ethanol are mixed.

Solution 16-50-150 mg (0.06-0.18 mmole) paclitaxel is dissolved in 5-10 ml methylene chloride. The solution is added to 30 ml of human serum albumin solution (5% w/v). The solution is then homogenized for 5 minutes at low speed to form an emulsion. The emulsion is then sonicated at 40 kHz at 50-90% power at 0 to 5 degrees C. for 1 to 5 min.

Solution 17-50-150 mg (0.05-0.16 mmole) rapamycin is dissolved in 5-10 ml methylene chloride and 10-30 mg p-isononylphenoxypolyglycidol. The solution is added to 30 ml of human serum albumin solution (5% w/v). The solution is then homogenized for 5 minutes at low speed to form an emulsion. The emulsion is then sonicated at 40 kHz at 50-90% power at 0 to 5 degrees C. for 1 to 5 min.

Example 2

PTCA balloon catheters (3 mm in diameter and 20 mm in length) are folded with three wings under vacuum. The folded balloon under vacuum is sprayed or dipped in a solution (1-17) in example 1. The folded balloon is then dried, sprayed or dipped again, dried again, and sprayed or dipped again until sufficient amount of drug on the balloon (3 microgram per square mm) is obtained. The coated folded balloon is then rewrapped and sterilized for animal testing.

Example 3

5 PTCA balloon catheters (3 mm in diameter and 20 mm in length) are folded with three wings under vacuum. The folded balloon under vacuum is sprayed or dipped in a solution (1-5) in example 1. The folded balloon is then dried, sprayed or dipped again in a solution (6-10), dried, and sprayed or dipped again until sufficient amount of drug on the balloon (3 microgram per square mm) is obtained. The coated folded balloon is then rewrapped and sterilized for animal testing.

Example 4

5 PTCA balloon catheters crimped with bare metal coronary stent (3 mm in diameter and 20 mm in length) are sprayed or dipped in a solution (1-5) in example 1. The stent delivery system is then dried, sprayed or dipped again in a solution (6-10), dried and sprayed or dipped again until sufficient amount of drug on the stent and balloon (3 microgram per square mm) is obtained. The coated folded stent delivery system is then sterilized for animal testing.

Example 5

Drug coated balloon catheters and uncoated balloon catheters (as control) are inserted into coronary arteries in pigs. The balloon is over dilated (1:1.2), and the inflated balloon is held in the vessel for 60 seconds to release drug, then deflated and withdraw from the pig. The animals are angiographed after 3 days, 31 days, 3 months, 6 months, 9 months and 12 months. The amount of drug in the artery tissues of the sacrificed animal is measured after 60 minutes, 3 days, 31 days, 3 months, 6 months, 9 months and 12 months.

Example 6

5 coronary stents (3 mm in diameter and 18 mm in length) are spray or dip coated with the solution (1-17) in example 1. The stents are then dried, sprayed or dipped again, and dried again until a sufficient amount of drug on the stent (3 microgram per square mm) is obtained. The coated stent is then crimped on PTCA balloon catheters (3 mm in diameters and 20 mm in length). The coated stents with balloon catheters are then sterilized for animal testing.

Example 7

The drug coated stent and uncoated stent (as control) are inserted into coronary arteries in pigs, then the balloon is over dilated (1:1.2). The stent is implanted and drug released, and the balloon is deflated and withdraw from the pig. The animals are then angiographed after 5, 30, 60 minutes, 3 days, 31 days, 3 months, 6 months, 9 months and 12 months. The amount of drug in the artery tissues of the sacrificed animal is measured 60 minutes, 1 day, 3 days, 31 days, 3 months, 6 months, 9 months and 12 months.

Example 8

5 PTCA balloon catheters are sprayed or dipped in the solution (1-17) in example 1, dried, and sprayed or dipped and dried again until sufficient amount of drug on balloon is obtained (3 microgram per square mm) is obtained. A bare metal coronary stent (3 mm in diameter and 20 mm in length) is crimped on each coated balloon. The coated balloons with crimped bare metal stents are then wrapped and sterilized for animal test.

Example 9

5 PTCA balloon catheters are sprayed or dipped in a solution (1-5) in example 1, dried, and sprayed or dipped again in a solution (6-10). Balloons are then dried and sprayed or dipped again until sufficient amount of drug on the balloon (3 microgram per square mm) is obtained. A bare metal coronary stent (3 mm in diameter and 20 mm in length) is crimped on each coated balloon. The coated balloons with crimped bare metal stents are then wrapped and sterilized for animal test.

Example 10

The drug coated balloon-expandable bare metal stent of Example 8 and 9 and plain balloon-expandable bare metal stent (as control) are inserted into coronary arteries in pigs, and the balloon is over dilated (1:1.2). Stent is implanted, and the balloon is held inflated for 60 seconds to release drug, and the balloon is deflated and withdraw from the pig. The animals are then angiographed after 5, 30, 60 minutes, 3 days, 31 days, 3 months, 6 months, 9 months and 12 months. The amount of drug in the artery tissues of the sacrificed animal is measured after 60 minutes, 1 day, 3 days, 31 days, 3 months, 6 months, 9 months and 12 months.

Example 11

150 mg (0.18 mmole) paclitaxel, 5 ml acetone (or ethylacetate or methyl ethyl ketone), 150 mg acetic anhydride or maleic anhydride or diglycolic anhydride and 0.5 ml ethanol are mixed, then stirred until a solution is obtained. 5 PTCA balloon catheters are sprayed or dipped in the solution, dried, and sprayed or dipped again until sufficient amount of drug on the balloon (3 microgram per square mm) is obtained. The coated balloon is then treated under high pH (range pH 8-11.5) conditions to hydrolyze the anhydride. This can be confirmed by IR method. The hydrophilicity of the coating is now increased. The coated balloons are then sterilized for animal test.

Example 12

The drug coated balloon catheters and uncoated balloon catheters (as control) are inserted via a bronchoscope into the pulmonary airway in pigs. The balloon is dilated, and the inflated balloon is held expanded in the lumen for 60 seconds to release drug. The balloon is deflated and withdrawn from the pig. The animals are then examined bronchoscopically and tissues samples are taken for pathology and quantification of drug uptake after 3 days, 31 days, 3 months, 6 months, 9 months and 12 months.

Example 13

The uncoated stent delivery catheters are inserted into the vascular lumen in pigs. The balloon is dilated, the stent is deployed and the deflated balloon is the withdrawn. The pharmaceutical solution 1-15 of example 1 (10-100 ml) is injected (about 5-15 mg drug per pig) at the site of stent implantation. The drug is then absorbed by injured tissue. The animals are then examined and tissues samples are taken for pathology.

Example 14

The diseased tissue (breast cancer or atheroma or stenosis) is removed surgically from a human body. The pharmaceutical solution 1-15 of example 1 (10-100 ml) is then injected into or onto the surgical cavities created by the surgical intervention (about 5-20 mg drug). The local drug delivery includes injection by long needle, guide catheters, introducer shealth, drug infusion tube and other drug delivery catheters. The drug is then absorbed by tissue at the target site.

What is claimed is:

1. A method for preparing a drug coated balloon catheter, the method comprising:
   (a) preparing a solution comprising:
     an organic solvent selected from the group consisting of hexane, octane, cyclohexane, heptane, benzene, toluene, xylene, methanol, ethanol, propanol, isopropanol, diethylamide, ethylene glycol monoethyl ether, Trascutol, benzyl alcohol, dioxane, dimethyl ether, tetrahydrofuran, ethyl acetate, isobutyl acetate, acetone, acetonitrile, diethyl ketone, methyl ethyl ketone, dimethylformamide, dimethylsulfoxide, mixtures of water and ethanol, mixtures of water and acetone, mixtures of water and methanol, mixtures of water and tetrahydrofuran, and combinations thereof;
     a therapeutic agent selected from the group consisting of paclitaxel, rapamycin, and mixtures thereof;
     at least one first additive selected from the group consisting of PEG sorbitan monolaurates, PEG sorbitan monooleates, and mixtures thereof; and
     at least one additional additive selected from the group consisting of sorbitol, sorbitan, gluconolactone, and mixtures thereof;
   (b) forming a coating layer containing the therapeutic agent and the at least one additive on an exterior surface of a balloon of a balloon catheter to form the drug coated balloon catheter by:
     (i) applying the solution to the balloon in an inflated or partially inflated state; and
     (ii) drying the balloon to evaporate the organic solvent from the coating solution after the solution is applied; and
   (c) deflating and folding the balloon,
   wherein the ratio by weight of the additives to the therapeutic agent in the coating layer is from 0.05 to 100.

2. The method according to claim 1, wherein the thickness of the coating layer is from about 0.1 µm to 200 µm.

3. The method according to claim 1, wherein the ratio by weight of the additives to the therapeutic agent in the coating layer is from 0.1 to 5.

4. The method according to claim 1, wherein the ratio by weight of the additives to the therapeutic agent in the coating layer is from 0.8 to 1.2.

5. The method according to claim 1, wherein the at least one additional additive is selected from the group consisting of sorbitol, sorbitan, and mixtures thereof.

6. The method according to claim 1, wherein the at least one first additive is selected from the group consisting of PEG-20 sorbitan monolaurate and PEG-20 sorbitan monooleate.

7. The method according to claim 1, wherein:
   the at least one first additive is selected from the group consisting of PEG-20 sorbitan monolaurate and PEG-20 sorbitan monooleate; and
   the at least one additional additive is selected from the group consisting of sorbitol, gluconolactone, and mixtures thereof.

8. The method according to claim 7, wherein the solution consists essentially of the organic solvent, the therapeutic agent, the at least one first additive, and the at least one additional additive.

9. The method according to claim 7, wherein the solution consists essentially of:
   the organic solvent;
   from 1% to 15% total by weight, based on the total weight of the solution, of the at least one first additive and the at least one additional additive; and
   from 2% to 20% total by weight, based on the total weight of the solution, of the therapeutic agent, the at least first one additive, and the at least one additional additive.

10. The method according to claim 9, wherein the organic solvent is selected from the group consisting of ethanol; mixtures of water and ethanol; acetone; mixtures of water and acetone; mixtures of acetone and ethanol; and mixtures of water, acetone, and ethanol.

11. The method according to claim 1, wherein (b)(i) and (b)(ii) are repeated until a therapeutically effective amount of the therapeutic agent in the coating layer is deposited on the exterior surface of the balloon.

12. The method according to claim 1, wherein (b)(i) and (b)(ii) are repeated until the exterior surface of the balloon has thereon a concentration density of therapeutic agent of from 1 µg/mm$^2$ to 20 µg/mm$^2$.

13. The method according to claim 1, wherein the solution comprises:
   from 0.5% to 50% by weight, based on the total weight of the solution, of the therapeutic agent; and
   from 1% to 45% by weight, based on the total weight of the solution, of the additives.

14. The method according to claim 1, wherein the solution comprises a total of from 2% to 20% by weight, based on the total weight of the solution, of the therapeutic agent and additives in the organic solvent.

15. The method according to claim 1, wherein the organic solvent is selected from the group consisting of methanol, ethanol, propanol, isopropanol, acetone, dioxane, tetrahydrofuran, dimethylformamide, acetonitrile, dimethylsulfoxide, and combinations thereof.

16. The method according to claim 1, wherein the organic solvent is selected from the group consisting of ethanol; mixtures of water and ethanol; acetone; mixtures of water and acetone; mixtures of acetone and ethanol; and mixtures of water, acetone, and ethanol.

* * * * *